US008828432B2

(12) United States Patent
van Lengerich

(10) Patent No.: US 8,828,432 B2
(45) Date of Patent: Sep. 9, 2014

(54) EMBEDDING AND ENCAPSULATION OF SENSITIVE COMPONENTS INTO A MATRIX TO OBTAIN DISCRETE CONTROLLED RELEASE PARTICLES

(75) Inventor: Bernhard H. van Lengerich, Plymouth, MN (US)

(73) Assignee: General Mills, Inc., Minneapolis, MN (US)

( * ) Notice: Subject to any disclaimer, the term of this patent is extended or adjusted under 35 U.S.C. 154(b) by 1516 days.

(21) Appl. No.: 09/782,320

(22) Filed: Feb. 13, 2001

(65) Prior Publication Data

US 2002/0044968 A1 Apr. 18, 2002

Related U.S. Application Data

(62) Division of application No. 09/269,763, filed on May 17, 1999, now Pat. No. 6,190,591.

(60) Provisional application No. 60/029,038, filed on Oct. 28, 1996, provisional application No. 60/052,717, filed on Jul. 16, 1997.

(51) Int. Cl.
*A61K 9/00* (2006.01)
*A61K 9/26* (2006.01)
*C08B 30/00* (2006.01)

(52) U.S. Cl.
USPC .............. 424/469; 424/490; 424/408; 127/32

(58) Field of Classification Search
USPC ................. 424/489, 492, 498, 499, 502, 493; 426/516, 96, 560
See application file for complete search history.

(56) References Cited

U.S. PATENT DOCUMENTS

| | | | |
|---|---|---|---|
| 2,876,160 A | 3/1959 | Schoch et al. | |
| 3,027,102 A | 3/1962 | Lödige et al. | |
| 3,404,984 A | 10/1968 | Olsen | |
| 3,762,931 A * | 10/1973 | Craig et al. | |
| 3,786,123 A | 1/1974 | Katzen | |
| 3,868,471 A | 2/1975 | Decelles et al. | |
| 3,922,354 A | 11/1975 | Galluzzi et al. | |
| 3,925,343 A * | 12/1975 | Hampton et al. | |
| 3,928,567 A | 12/1975 | Andersen et al. | |
| 3,962,416 A | 6/1976 | Katzen | |
| 3,992,555 A | 11/1976 | Kovacs | |
| 4,075,356 A | 2/1978 | Haag et al. | |
| 4,106,991 A | 8/1978 | Markussen et al. | |
| 4,178,392 A | 12/1979 | Gobble et al. | |
| 4,187,321 A * | 2/1980 | Mutai et al. ..................... | 426/43 |
| 4,242,219 A | 12/1980 | Bogerman et al. | |
| 4,357,358 A * | 11/1982 | Schanze | |
| 4,379,171 A | 4/1983 | Furda et al. | |
| 4,386,106 A | 5/1983 | Merritt et al. | |
| 4,532,145 A | 7/1985 | Saleeb et al. | |
| 4,689,235 A | 8/1987 | Barnes et al. | |
| 4,738,724 A * | 4/1988 | Wittwer et al. ............ | 106/206.1 |
| 4,755,397 A * | 7/1988 | Eden et al. ................. | 427/213.3 |
| 4,816,259 A | 3/1989 | Matthews et al. | |
| 4,820,534 A | 4/1989 | Salgeb et al. | |
| 4,871,574 A | 10/1989 | Yamazaki et al. | |
| 4,886,820 A | 12/1989 | Gross et al. | |
| 4,888,171 A | 12/1989 | Okonogi et al. | |
| 4,888,174 A * | 12/1989 | Farquharson et al. .......... | 514/89 |
| 4,911,952 A | 3/1990 | Doane et al. | |
| 4,938,967 A * | 7/1990 | Newton et al. ................. | 424/458 |
| 4,999,208 A | 3/1991 | Lengerich et al. | |
| 5,009,900 A | 4/1991 | Levine et al. | |
| 5,023,083 A | 6/1991 | Drell | |
| 5,064,669 A | 11/1991 | Tan et al. | |
| 5,071,668 A | 12/1991 | van Lengerich et al. | |

(Continued)

FOREIGN PATENT DOCUMENTS

DE 37 38 042 A 5/1988
DE 40 21 678 1/1992

(Continued)

OTHER PUBLICATIONS

Stedman's Medical Dictionary 25$^{th}$ Go. p. 1258, 1990.*
Per Artusson et al., "Characterization of Polyacryl Starch Microparticles as Carriers for Proteins and Drugs," *Journal of Pharmaceutical Science*, vol. 73, No. 11, pp. 1507-1513 (Nov. 1984).
Lennart Randen et al., "Coprecipitation of Enzymes with Water Soluble Starch—An Alternative to Freeze-drying," *J. Pharm. Pharmacol.*, vol. 40, pp. 763-766 (1988).
Shigeaki Maruo et al., "Effects of Moranoline, 4-*O*-α-D-Glucopyranosylmoranoline and Their *N*-Substituted Derivatives on Thermostability of Cyclodextrin Glycosyltransferase, Glucoamylase, and β-Amylase," *Biosci. Biotech. Biochem.*, vol. 57, No. 8, pp. 1294-1298, (1993).
Wendell Q. Sun et al., "Protein stability in the amorphous carbohydrate matrix: relevance to anhydrobiosis," *Biochimica et Biophysica Acta*, vol. 1425, pp. 245-254 (1998).

(Continued)

*Primary Examiner* — Lezah Roberts
(74) *Attorney, Agent, or Firm* — Rachel A. Kahler; Barry I. Hollander

(57) ABSTRACT

Controlled release, discrete, solid particles which contain an encapsulated and/or embedded component such as a heat sensitive or readily oxidizable pharmaceutically, biologically, or nutritionally active component are continuously produced without substantial destruction of the matrix material or encapsulant. A release-rate controlling component is incorporated into the matrix to control the rate of release of the encapsulant from the particles. The additional component may be a hydrophobic component or a high water binding capacity component for extending the release time. The plasticizable matrix material, such as starch, is admixed with at least one plasticizer, such as water, and at least one release-rate controlling component under low shear mixing conditions to plasticize the plasticizable material without substantially destroying the at least one plasticizable material and to obtain a substantially homogeneous plasticized mass. The plasticizer content is substantially reduced and the temperature of the plasticized mass are substantially reduced prior to admixing the plasticized mass with the encapsulant to avoid substantial destruction of the encapsulant and to obtain a formable, extrudable mixture. The mixture is extruded through a die without substantial or essentially no expansion and cut into discrete, relatively dense particles. Release properties may also be controlled by precoating the encapsulant and/or coating the extrudate particles with a film-forming component.

51 Claims, 6 Drawing Sheets

(56) References Cited

U.S. PATENT DOCUMENTS

| | | | |
|---|---|---|---|
| 5,074,902 A | 12/1991 | Connick, Jr. et al. | |
| 5,075,058 A | 12/1991 | Chan et al. | |
| 5,079,012 A | 1/1992 | Lengerich et al. | |
| 5,087,461 A | 2/1992 | Levine et al. | |
| 5,095,054 A * | 3/1992 | Lay et al. | 524/47 |
| 5,106,639 A | 4/1992 | Lee et al. | |
| 5,118,513 A | 6/1992 | Mehansho et al. | |
| 5,183,690 A | 2/1993 | Carr et al. | |
| 5,262,167 A * | 11/1993 | Vegesna et al. | |
| 5,279,844 A | 1/1994 | Wesdorp et al. | |
| 5,296,000 A | 3/1994 | Darmont et al. | |
| 5,308,636 A * | 5/1994 | Tye et al. | 426/573 |
| 5,314,692 A | 5/1994 | Haarasilta et al. | |
| 5,320,669 A | 6/1994 | Lim et al. | |
| 5,338,560 A | 8/1994 | Wesdorp et al. | |
| 5,397,834 A * | 3/1995 | Jane et al. | 525/54.1 |
| 5,431,929 A | 7/1995 | Yatka et al. | |
| 5,449,708 A * | 9/1995 | Schiltz | 524/47 |
| 5,451,673 A * | 9/1995 | Fishman et al. | 536/123 |
| 5,458,823 A | 10/1995 | Perkins et al. | |
| 5,462,982 A | 10/1995 | Bastioli et al. | |
| 5,466,460 A | 11/1995 | McMahon et al. | |
| 5,508,053 A | 4/1996 | Villota et al. | |
| 5,512,311 A | 4/1996 | Capitani et al. | |
| 5,514,387 A | 5/1996 | Zimmerman et al. | |
| 5,597,416 A | 1/1997 | Fuisz et al. | |
| 5,683,720 A | 11/1997 | Myers et al. | |
| 5,716,615 A * | 2/1998 | Cavaliere-Vesely et al. | |
| 5,744,180 A | 4/1998 | Cherukuri et al. | |
| 5,750,104 A | 5/1998 | Sipos | |
| 5,804,208 A * | 9/1998 | Andersch et al. | 424/407 |
| 5,820,903 A | 10/1998 | Fleury et al. | |
| 5,851,553 A | 12/1998 | Myers et al. | |
| 5,852,114 A * | 12/1998 | Loomis et al. | 525/57 |
| 5,862,998 A | 1/1999 | Bogue et al. | |
| 5,894,029 A | 4/1999 | Brown et al. | |
| 5,902,617 A | 5/1999 | Pabst | |
| 5,939,127 A | 8/1999 | Abboud | |
| 5,952,033 A | 9/1999 | Anantharaman et al. | |
| 5,958,502 A | 9/1999 | Fulger et al. | |
| 5,972,373 A | 10/1999 | Yajima et al. | |
| 5,972,404 A | 10/1999 | van Lengerich | |
| 5,972,415 A | 10/1999 | Brassart et al. | |
| 5,976,603 A | 11/1999 | Kota et al. | |
| 6,004,594 A | 12/1999 | van Lengerich | |
| 6,008,027 A | 12/1999 | Langner | |
| 6,011,092 A * | 1/2000 | Seppala et al. | 524/47 |
| 6,024,994 A | 2/2000 | Jacobson et al. | |
| 6,048,551 A | 4/2000 | Amidon et al. | |
| 6,149,965 A | 11/2000 | van Lengerich et al. | |
| 6,168,811 B1 | 1/2001 | Clark et al. | |
| 6,174,553 B1 | 1/2001 | Cerda et al. | |
| 6,190,591 B1 | 2/2001 | van Lengerich | |
| 6,242,033 B1 | 6/2001 | Sander | |
| 6,261,613 B1 | 7/2001 | Narayanaswamy | |
| 6,290,990 B1 * | 9/2001 | Grabowski et al. | 424/499 |
| 6,342,257 B1 | 1/2002 | Jacobson et al. | |
| 6,436,453 B1 | 8/2002 | van Lengerich et al. | |
| 6,468,568 B1 | 10/2002 | Leusner et al. | |
| 6,500,463 B1 | 12/2002 | van Lengerich | |
| 6,723,358 B1 | 4/2004 | van Lengerich | |
| 6,837,682 B2 | 1/2005 | Evanson et al. | |
| 7,431,986 B2 | 10/2008 | Van Lengerich et al. | |
| 2001/0008635 A1 | 7/2001 | Quellet et al. | |
| 2001/0044026 A1 | 11/2001 | Vaghefi et al. | |
| 2002/0044968 A1 | 4/2002 | van Lengerich et al. | |

FOREIGN PATENT DOCUMENTS

| | | |
|---|---|---|
| DE | 40 41 752 A1 | 6/1992 |
| DE | 19503993 * | 8/1996 |
| EP | 33662 A | 10/1969 |
| EP | 0 202 409 A2 | 11/1986 |
| EP | 0 223 963 A | 6/1987 |
| EP | 0 347 014 A1 | 12/1989 |
| EP | 0 385 081 A2 | 9/1990 |
| EP | 391518 A | 10/1990 |
| EP | 0400531 | 12/1990 |
| EP | 0404727 * | 12/1990 |
| EP | 0 462 012 A2 | 12/1991 |
| EP | 0 465 364 A1 | 11/1992 |
| EP | 552057 A | 7/1993 |
| EP | 603992 A1 | 6/1994 |
| EP | 605913 A | 7/1994 |
| EP | 0 705 541 A1 | 4/1996 |
| EP | 1 064 856 A2 | 1/2001 |
| EP | 1066761 A2 | 1/2001 |
| EP | 1 118 274 A | 7/2001 |
| FR | 2 640 472 A | 6/1990 |
| FR | 2 758 055 | 7/1998 |
| GB | 15312 | 3/1911 |
| GB | 1 437 501 A | 5/1976 |
| JP | 47014316 A | 5/1972 |
| JP | 59139317 A | 8/1984 |
| JP | 60075226 A | 4/1985 |
| JP | 63 173568 | 7/1988 |
| JP | 1313421 A | 12/1989 |
| JP | 6024962 A | 2/1994 |
| JP | 2000139372 A | 5/2000 |
| WO | WO 85/04074 | 9/1985 |
| WO | WO 88/01512 A | 3/1988 |
| WO | WO 90/15537 | 12/1990 |
| WO | 91 03940 | 4/1991 |
| WO | WO 92/00130 | 1/1992 |
| WO | WO 92/00140 | 1/1992 |
| WO | WO 92/12645 | 8/1992 |
| WO | WO 94/01001 | 1/1994 |
| WO | WO 94/23593 | 10/1994 |
| WO | WO94/26883 | 11/1994 |
| WO | WO 95/00121 | 1/1995 |
| WO | WO 95/18544 | 7/1995 |
| WO | WO 95/26752 | 10/1995 |
| WO | 96 09773 | 4/1996 |
| WO | 96 14058 | 5/1996 |
| WO | WO 97/16076 | 5/1997 |
| WO | WO 97/39116 | 10/1997 |
| WO | WO 98/18610 | 5/1998 |
| WO | WO 98/50019 A | 11/1998 |
| WO | WO 98/54980 | 12/1998 |
| WO | WO 99/11242 A1 | 3/1999 |
| WO | WO 99/20745 A1 | 4/1999 |
| WO | WO 99/23896 | 5/1999 |
| WO | WO 99/34688 | 7/1999 |
| WO | WO 99/45904 A1 | 9/1999 |
| WO | WO 99/48372 | 9/1999 |
| WO | WO 99/56563 | 11/1999 |
| WO | WO 99/61002 A1 | 12/1999 |
| WO | WO 00/21504 | 4/2000 |
| WO | WO 00/41740 A2 | 7/2000 |
| WO | WO 00/64436 A1 | 11/2000 |
| WO | WO 01/25414 A1 | 4/2001 |
| WO | WO 01/74175 A1 | 10/2001 |

OTHER PUBLICATIONS

Colonna et al., "Extrusion Cooking of Starch & Starchy Products," *Extrusion Cooking*, C. Mercier, et al. AACC, St. Paul, MN (1989), pp. 247-319.

Meuser et al., "A Systems Analytical Approach to Extrusion," *Food Extrusion Science & Technology*, ed. J. Kokini, Dekker Publ. (1992), pp. 619-630.

Brochure entitled "Innovate With Raftiline®," Orafti Active Food Ingredients, Nov. 1996.

"Inulin-A 'Good-for-you' Fat Replacer, Texture Modifier," *Food Formulating*, p. 15, Feb. 1997.

Brighenti, F., et al., "One Month Consumption of Ready-to-eat Breakfast Cereal Containing Inulin Markedly Lowers Serum Lipids in Normolipidemic Men," from: Proceedings of 7th FENS European Nutrition Conference, 1995.

Silva, R., "Use of Inulin as a Natural Texture Modifier," *Cereal Foods World*, Oct. 1996, vol. 41, No. 10, pp. 792-794.

Niness, "Breakfast Foods and the Health Benefits of Inulin and Oligofructose", *Cereal Foods world*, vol. 44, No. 2, Feb. 1999, pp. 79-81.

(56) References Cited

OTHER PUBLICATIONS

Arshady R., "Microcapsules for Food," *Journal of Microencapsulation*, vol. 10, No. 4, pp. 413-435, Oct. 1, 1993, Taylor and Francis Inc., London, GB.

U.S. Appl. No. 09/233,443, filed Jan. 20, 1999, van Lengerich.

U.S. Appl. No. 11/263,360, filed Oct. 31, 2005, van Lengerich et al.

*Webster's New Collegiate Dictionary,* 1986 ed., pp. 442 ("extrude"), 542 ("gum"), 740 ("melt"), 764 ("molten") and 1111 ("slurry").

The Scots Kitchen, Abemethy biscuits recipe from the web site www.scotweb.com.uk/kitchen/BAK/abemethy.html, based upon "A Taste of Old Scotland" by Micheil Rob Mack Phadruig, last updated May 24, 1999.

Hermann, "Specialty Dairy Ingredients", Food Product Design, Feb. 1992.

"Starch's many variants", by Meattech, *Food Engineering and Ingredients,* pp. 58-60 (May 2006).

Kempf, "Process for the Industrial Production of wheat Starch From Whole Wheat", *Wheat Is Unique,* Washington State University, Pullman, WA, pp. 521-540.

Cornell et al., "The Wet Milling of Wheat Flour", *Wheat Chemistry and Utilization,* pp. 79-125.

Johnson et al., "Wet Milling: The Basis for Corn Biorefineries", *Corn: Chemistry and Technology,* Second Edition, Am. Assn. of Cereal Chemists, Inc., St. Paul, MN, pp. 449-494.

Leach, "Gelatinization of Starch", *Starch: Chemistry and Technology,* vol. I, Academic Press, 1965, pp. 289-307.

Whistler et al., "Starch", *Carbohydrate Chemistry for Food Scientists,* Eagan Press, St. Paul, MN, pp. 117-151.

Atwell et al., "The Terminology and Methodology Associated With Basic Starch Phenomena," *Cereal Foods World,* vol. 33, No. 3, pp. 306-311 (Mar. 1988)

Van Lengerich, Influence of Extrusion Processing on In-Line Rheological Behavior, Structure, and Function of Wheat Starch, Dough Rheology and Baked Product Texture, eh. Faridi et al. (eds). pp. 421-471, Van Nostrand Reinhold 1990.

\* cited by examiner

EMBEDDING AND ENCAPSULATION OF SENSITIVE COMPONENTS INTO A MATRIX TO OBTAIN DISCRETE CONTROLLED RELEASE PARTICLES

This application is a Divisional of U.S. application Ser. No. 09/269,763, filed Apr. 12, 1999, now U.S. Pat. No. 6,190,591 which is a 371 of PCT/US97/18984 filed Oct. 27, 1997, which claims priority of U.S. Ser. No. 60/052,717, filed Jul. 16, 1997, and U.S. Ser. No. 60/029,038, filed Oct. 28, 1996.

FIELD OF THE INVENTION

The present invention relates to a continuous process for producing controlled release, discrete, solid particles which contain an encapsulated and/or embedded component such as a heat sensitive or readily oxidizable pharmaceutically, biologically, or nutritionally active component.

BACKGROUND OF THE INVENTION

In encapsulating a component in a matrix, the matrix material is generally heated to a sufficiently high temperature to provide a plasticized mass which facilitates coating of the component. Upon cooling, the matrix material hardens or becomes solidified and protects the encapsulant from undesirable or premature reaction. However, heating of the matrix to plasticize it or to form a melt may deleteriously affect or decompose the encapsulant as well as the matrix material. Additionally, the mixing or high shear used to disperse the encapsulant uniformly throughout the plasticized matrix material may likewise adversely affect the matrix material or encapsulant. Furthermore, the use of high temperatures to plasticize or melt the matrix material may cause evaporation and loss of the encapsulant. The addition of liquids to the matrix material to reduce its viscosity and to facilitate mixing may require excessive drying or evaporation of the plasticizing liquid for the attainment of a formable composition capable of being formed into discrete, substantially uniform pieces. Furthermore, removal of the plasticizing liquid may adversely expand the product, decrease its density, and make the encapsulated component more susceptible to attack or more easily released.

The production of expanded products is disclosed in European patent publication nos. EP 0465364 A1 (published Jan. 8, 1992) and EP 0462012 A2 (published Dec. 18, 1991), U.S. Pat. No. 3,962,416 to Katzen and U.S. Pat. No. 3,786,123 to Katzen. The two European patent publications disclose the production of an anti-obesity food and a method for making it by extrusion of starches with fatty acids into an expanded product having densities between 0.1 and 0.3 g/cm$^3$. U.S. Pat. No. 3,962,416 to Katzen discloses an expanded product which contains at least one nutrient and one gelatinized starch.

U.S. Pat. No. 3,786,123 to Katzen discloses a method for producing encapsulated nutrients using extrusion temperatures of between 250° F. and 400° F. and extrusion pressures of between 200 psi to 2500 psi. A high protein encapsulating agent containing up to 40% starch may be used. The starch is gelatinized and extruded into an expanded product.

However, in producing a product having controlled release or delayed release, excessive expansion or puffing may result in too rapid release properties or may undersirably expose an encapsulant to destructive reactions. For example, an edible composition for delivering encapsulated pharmaceutically or nutritionally active components or for a non-edible agricultural product for delivering biocides or herbicides, it is desirable that die products have a substantially spherical shape and a high density. Such products exhibit a substantially low ratio between surface area and volume and thus minimize or prevent surface related destructive reactions that occur upon exposure to air or oxygen and light. The spherical shapes and high densities also minimize the surface which would be available to expose embedded material which is not encapsulated. Furthermore, for edible products for delivering pharmaceutically or nutritionally active components, it is desirable that the products are capable of being consumed or swallowed without chewing or substantially no chewing. Avoiding the need for mastication, further assures that the products reach the digestive tract without substantial enzymatic hydrolysis in the mouth. Furthermore, it helps to control or reduce dissolution of the product in gastric juice and to control the release of the embedded or encapsulated components in the stomach and/or in the intestine.

International patent publication no. WO 92/00130 (published Jan. 9, 1992) discloses a continuous process for obtaining an encapsulated, biologically active product in a starchy matrix. A biologically active agent and starch are mixed before extrusion and extruded as a blend, with the encapsulant or biologically active agent being heated together with the starch. Alternatively, a core material to be encapsulated may be added and blended with an aqueous dispersion of starch after the starch and water have been subjected to an elevated temperature sufficient to gelatinize the starch. The extrusion process, it is disclosed, exposes the mix to high shear mechanical action at a temperature above the gelatinization temperature of the starch. The use of extrusion barrel temperatures of between about 58° C. and 98° C. are disclosed. While these barrel temperatures may be above the gelatinization temperature of starch, the extruder utilized has barrel sections that are only three l/d long. The screw speeds utilized, between 400 rpm and 200 rpm, result in a very short residence time of the blend inside the extruder and barely allow heating up of the starch water mix. As a result, the temperatures obtained are generally too low to obtain substantial gelatinization of native starches. Additionally, the barrel temperatures used are particularly too low for substantial gelatinization of high amylose starch which generally gelatinizes at temperatures substantially above 100° C., for example at 125° C. The use of extrusion barrel temperatures which are not sufficiently high to substantially or completely gelatinize the starch may not form a sufficiently continuous, plasticized and homogeneous matrix for effective embedding or encapsulation.

In addition, the use of relatively low extrusion temperatures, high speed mixing, and a high viscosity starch composition generally requires a high mechanical energy input. High shear is directly related to high specific mechanical energy, which in turn increases the molecular destructurization and dextrinization of starch. Breakdown of the starch molecules, and in particular the amylopectin, increases the solubility of the extruded starch composition in aqueous systems as described in P. Colonna, et al., "Extrusion Cooking of Starch & Starchy Products," *Extrusion Cooking*, C. Mercier, et al. pp. 247-319, AACC, St. Paul, Minn. (1989) and F. Meuser, et al, "A Systems Analytical Approach To Extrusion," *Food Extrusion Science & Technology*, ed. J. Kokini, Dekker Publ., pp. 619-630 (1992). Increased solubility of the extruded starch in aqueous systems decreases the stability of the product against moisture and subsequently diminishes or shortens the protection and controlled release of the embedded or encapsulated substances. In addition, subjecting the encapsulant to the same high shear and high temperature conditions to which the starch is subjected may adversely affect the encapsulant by at least partially destroying it or decomposing it into unknown solid or volatile substances.

Pregelatinized starch is used in numerous applications in the food industry as a swelling agent and for accelerated and extended water absorption in foods such as soups, sauces, instant puddings, baby food, and thickening agents. However, it has been found that the use of pregelatinized starch or the use of starch as the only matrix material during extrusion cooking generally results in a matrix which releases the encapsulant too quickly. It has been found that the penetration of water into a pure starch matrix causes early release of the encapsulant into the environment. Generally the time to release 100% of the encapsulant is too short to provide a desirable time-release or controlled-release which is effective for delivering the encapsulant at a desired location or time.

International patent publication no. WO 95/26752 (published Oct. 12, 1995) discloses the production of a food product for the enteric supply of a fatty acid, a fatty acid containing substance, an amino acid, or an amino acid containing substance by at least partially complexing the fatty acid or amino acid in the amylose helix of starch to mask the acid. The product may contain one or more flavors and colors, fat soluble substances, anti-oxidants, or pharmacologically effective substances. The components may be first dry mixed and subsequently fed into an extruder where they are substantially mixed and subsequently heated above the gelatinization temperature of the starch to obtain an elasticized mass which is extruded and formed into pellets. However, heat-sensitive components would be destroyed during the heating step.

International patent publication no. WO 85/04074 to Flashinski, et al. (published Sep. 26, 1985) discloses an insect bait containing an insect-controlling material in a gelatinized starch matrix. The bait is made by coextruding starch with the insect-controlling material at temperature and pressure conditions sufficient to cook and gelatinize the starch. Alternatively, a pregelatinized starch may be mixed with the insect-controlling material and water to form a gel. In the formation of the insect bait by mixing and extruding the components, it is disclosed, it is essential to utilize additives, including the insecticides and repellents which will withstand the extrusion temperatures of starch without the degradation or vaporization. The extrusion temperatures of the insect-bait mixture, depending upon the starch content and other additives, ranges between about 160 to about 310° F. at pressures of from about 300 through 800 psi.

U.S. Pat. No. 5,183,690 to Carr, et al. discloses a continuous process for imparting predetermined release properties to an encapsulated biologically active agent in a matrix of starchy material. The starchy material, an active agent, and water are continuously blended in an ingredient stream wherein the starchy material is at a solids concentration of at least 40%. The ingredients stream is continuously extruded as an extrudate and the extrudate is continuously recovered. The conditions of blending, extruding, and recovering are preselected to yield the predetermined release properties. The temperature is elevated to at least about 65° C. to effect gelatinization of starch and assure an essentially molecular dispersion of the starch in the water. Alternatively, the core material to be encapsulated is added and blended with the aqueous dispersion of starch after the starch and water has been subjected to an elevated temperature sufficient to gelatinize the starch. In this embodiment the aqueous starch stream containing gelatinized starch may be lowered to a temperature as low as about 25° C. before the core material to be encapsulated is added and subjected to high-shear mechanical action. Under such low temperature conditions of admixture it is disclosed, the activity of sensitive biological material, such as bacteria and viruses, is preserved and loss of volatile organic materials is minimized. The rate of swelling of the products in water and the rate of release of active agents are controlled by altering the amount of water present in the starch-agent-water blend during processing. As the amount of water is decreased, both the swelling rate and the release rate increase. The rate of swelling of the products in water and the rate of release of active agent are also controlled by passage of the extrudate containing starch-agent-water through an exit die of various dimensions. As the exit die is reduced in size, both the rate and extent of swelling increase and the rate of release of agent increases.

The present invention provides a controlled release particulate composition which contains a hydrophobic component for controlling the release of an encapsulated and/or embedded active component from a plasticized matrix. High water binding capacity agents may also be used to delay or control the release of the encapsulant from the matrix. Furthermore, in the process of the present invention the amount of plasticizer is high to facilitate plasticization of the matrix material at low shear and is then reduced prior to adding the encapsulant to facilitate subsequent forming and to reduce post extrusion drying. The controlled release or delayed release composition may be produced without substantial expansion of the matrix material to thereby avoid production of a low density product which prematurely or too rapidly releases the encapsulant or the embedded component. The products may be produced using low shear mixing to avoid decomposition of the matrix material and encapsulant or active component. However, even though low shear mixing is utilized, substantial plasticization of the matrix material and at least substantially uniform distribution of the active component are achieved. Edible products produced in accordance with the present invention for delivering pharmaceutically or nutritionally active components may be consumed or swallowed without chewing so that the products may reach the digestive tract without substantial enzymatic hydrolysis in the mouth. In addition, in embodiments of the invention, the substantially spherical shape and high density of the products reduce or prevent substantial surface related destruction of the active components upon exposure of the particles to air, oxygen, light, or water. Timing of the release of the embedded or encapsulated component so that it is delayed until the product reaches the stomach and/or the intestine may be controlled by the use of varying amounts and types of hydrophobic components or high water holding capacity components in the plasticized matrix. The processes of the present invention may be used for the continuous production of an edible composition for delivering pharmaceutically or nutritionally active components, or for the production of an agricultural product for the controlled release of biocides, herbicides, fertilizers, growth stimulators, pesticides, or products for other uses such as, for example, detergents which release chemical and/or biological agents.

SUMMARY OF THE INVENTION

The present invention provides a continuous process for producing controlled release, discrete, solid particles which contain an encapsulated and/or embedded component. The particles comprise a matrix material in which the active component is encapsulated or embedded. The matrix material is plasticized upon heating to form a melt. The active component is admixed with the melt without substantially deleteriously affecting or decomposing the encapsulant or the matrix material. The active component is admixed with the plasticized matrix material at low temperatures and under low shear mixing conditions to thereby avoid substantial destruction of or volatilization of active components. Additionally, high water contents may be employed so as to substantially reduce viscosity and facilitate substantial gelatinization of the starch without substantially destroying the starch molecules. Subsequent removal of at least part of the water prior to adding the encapsulant avoids excessive drying or evaporation of the plasticizing liquid which may adversely affect the encapsulant content. The moisture reduction within the extruder also provides for the attainment of a formable composition capable of being formed into discrete, substantially uniform pieces. Extrusion of the matrix and active component blend may be performed without substantial expansion of the product thereby providing a high density product which is less susceptible to attack by aqueous or oxygen-containing mediums thereby providing a prolonged release time. The process of the present invention may be used to encapsulate heat sensitive components or readily oxidizable components, for example, pharmaceutically or biologically or nutritionally active components, without substantially destroying their activity. The products of the present invention may be edible for direct consumption or for incorporation into food products. In other embodiments of the invention, products, such as chemical or agricultural products such as pesticides, herbicides, fungicides, insecticides, rodenticides, or other products like detergents or flavorants, fragrances, and the like may be advantageously embedded or encapsulated to control or delay their release from their surrounding matrix.

In embodiments of the present invention, at least one additional ingredient or component may be used to control the release properties of the final product. The additional component may manage, control or affect the flow, diffusion or distribution of water or aqueous-based compositions into and within the final product particles. The additional ingredient or component for controlling the rate of release of the encapsulant may be a hydrophobic agent such as polyethylene, polyurethane, polypropylene, polyvinylchloride, polyvinylacetate, a fat, oil, wax, fatty acid, or emulsifier which increases the hydrophobicity of the matrix. The increased hydrophobicity helps to prevent or delays penetration of water or gastric juice into the matrix. Other ingredients which may be used to control the rate of the release are components which have a high water binding capacity which delay or prevent a fast dissolving of the matrix and thereby delay the release of the encapsulant into the matrix. Exemplary of high water binding capacity components which may be used are proteins, such as wheat gluten, gelatin, and casein, hydrocolloid gums, and the like.

In embodiments of the invention, matrix components may be added to increase the rate of release of the encapsulant. These rate increasing components may dissolve more readily in water than does another matrix material. Upon dissolution, permeability of the particles is increased, thereby increasing access to the encapsulant by the penetrating aqueous-based solvent.

In accordance with the method of the present invention, at least one plasticizable, matrix-forming material such as starch or polyvinylpyrrolidone may be admixed with a sufficient amount of a plasticizer such as water to reduce the melt or glass transition temperature of the plasticizable material, together with the additional release-rate controlling ingredient. The mix is heated above the melt or glass transition temperature of the plastifiable or matrix material, such as above the gelatinization temperature of a starch matrix ingredient, while conveying and mixing the ingredients within an extruder. The temperature is maintained sufficiently high for a sufficiently long period of time to at least partially gelatinize starch in the mixture. The additional ingredient which is used to control the rate of release of the encapsulant may be added before or after heating of the matrix material, such as starch.

After the matrix material is plasticized at a high moisture content to minimize molecular breakdown, at least some of the moisture may then be removed from the plasticized mass or cooked dough. The temperature of the plasticized mass may be reduced either by the moisture removal and/or by additional barrel cooling, the addition of inert gas, or by combinations of the above cooling methods. The plasticized or gelatinized mass having a reduced moisture content and lower temperature, is then conveyed toward a subsequent extruder barrel section while maintaining sufficiently low temperature to admix the encapsulant without thermally destroying the encapsulant. The encapsulant is admixed with the plasticized matrix under low temperature, low shear mixing conditions to distribute, coat, embed, or encapsulate the added active ingredient in the plasticized matrix material. Mixing is continued towards the extruder die while adjusting the product temperature for sufficient formability.

The admixture is extruded through the extrusion die and cut or otherwise formed into pieces or pellets with no or substantially no expansion of the extrudate. The extrudate or pieces may then be dried and then surface treated with a film-building substance to further encapsulate the extruded pellets or pieces. The film-building substance may also contain additional components that delay or prevent the access of light, oxygen, and/or water to the matrix. In embodiments of the invention, the one or more pharmaceutically, nutritionally, biologically or, chemically active ingredients may be pre-coated with a coating material such as shellac, zein, chitosan, chitin, an emulsifier or the like to further control the release properties of the encapsulant from the matrix material.

The products of the present invention may be in the form of discrete particles, pellets, or tablets. They may be spherical in shape, curvilinear or lens-shaped, flat discs, oval shaped, or the like. The diameter of the particles may range from about 0.5 mm to about 7 mm and the l/d ratio may be from about 0.1 to about 10. The specific density of the pellets or particles may be from about 800 g/liter to about 1500 g/liter.

The amount of plasticizer such as water admixed with the matrix material such as starch to form a plasticized mass may range from about 20% by weight to about 50% by weight, preferably from about 35% by weight to about 45% by weight, most preferably about 40% by weight, based upon the weight of the matrix material such as starch. The amount of the ingredient used to control the rate of release of the active component may range up to about 70% by weight, preferably from about 5% by weight to about 50% by weight, most preferably from about 10% by weight to about 35% by weight based upon the weight of the matrix material such as starch. The amount of the active component or encapsulant which may be encapsulated or embedded into the matrix may be from about 1% by weight to about 85% by weight, preferably from about 3% by weight to about 50% by weight, most preferably from about 5% by weight to about 20% by weight, based upon the weight of the matrix ingredient such as starch.

DETAILED DESCRIPTION OF THE INVENTION

Figure 1:
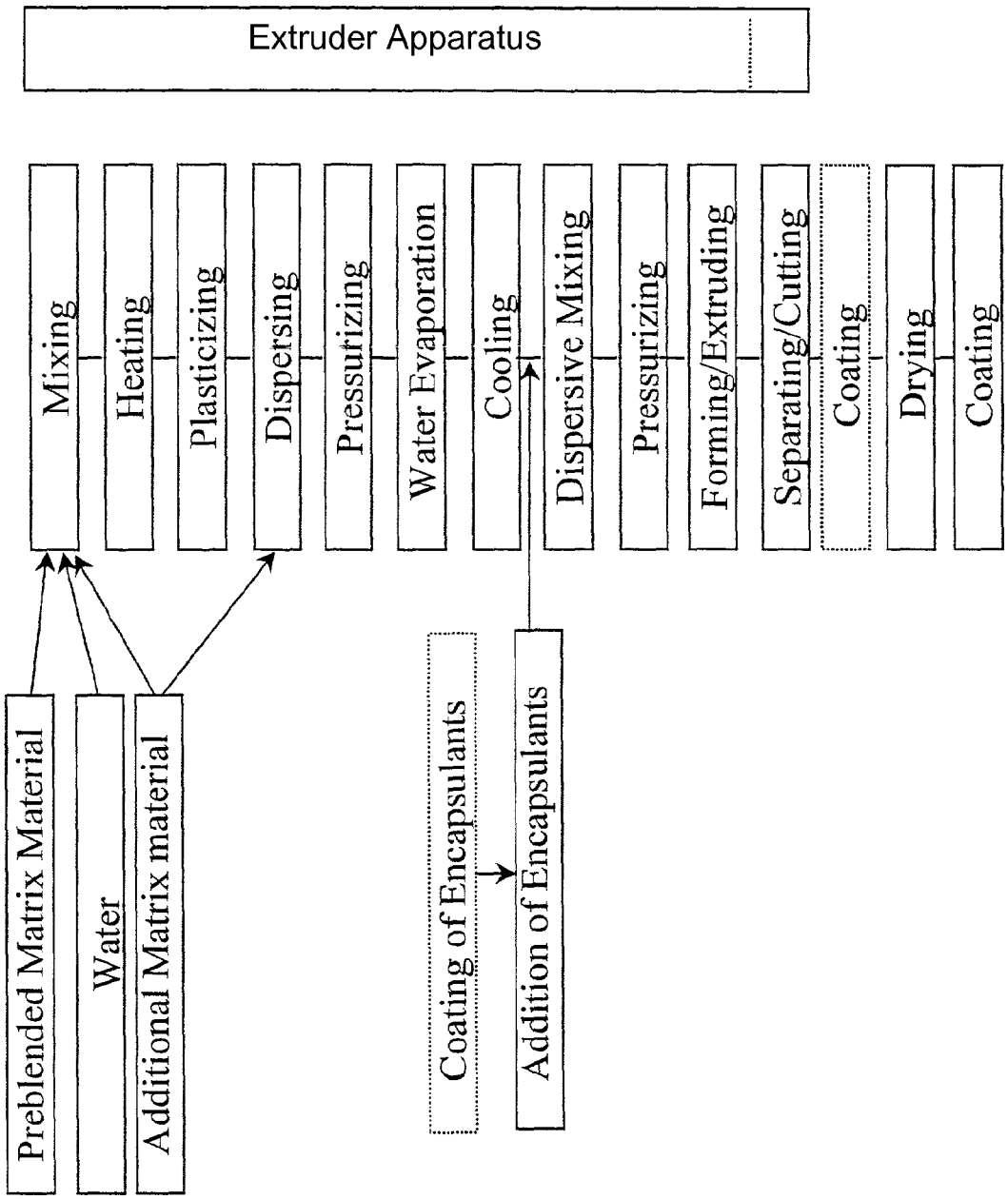
FIG. 1 shows a schematic representation of the process of the present invention.

An active component is encapsulated and/or embedded in a plasticizable matrix component or material in an continuous process to produce discrete, solid particles. Release of the active component from the matrix is delayed or controlled over time so that the active component is delivered when and where it is needed to perform its intended function. The release of the active component from the matrix may be controlled by an additional ingredient or additive which affects the hydrophobicity of the matrix or particle, the water binding capacity of the matrix or particle, the solubility or porosity of the matrix material or particle, or the glass transition ($T_g$) of the matrix material or particle. Pretreatment of the encapsulant, process conditions, and the final shape of the discrete particles may also be used to control the release of the active component from the matrix material. The continuous process of the present invention advantageously at least substantially uniformly distributes, embeds, or encapsulates the active component in the matrix material. The active components may be dispersed in the matrix material on a microscopic or molecular level. Active components which are dispersed on a molecular level may provide a higher bioavailability when released, as compared to their crystalline forms. The active components may be encapsulated or embedded either in a solid form or liquid form. The encapsulants and encapsulated products of the present invention may be edible such as pharmaceutically or biologically or nutritionally active components, or flavors or fragrances or they may be inedible compositions such as a detergent, herbicide, fungicide, pesticide, insecticide, or rodenticide, and the like. Release of the encapsulant from the matrix material may also be controlled by the use of a film or coating upon the encapsulant and/or upon the discrete, solid matrix-encapsulated particles.

The matrix material may be a plasticizable biopolymer such as a carbohydrate, such as a starch or cyclodextrin, or polymer such as polyvinylpyrrolidone or other non-hydrophobic polymers such as copolymers of N-vinylpyrrolidone (NVP) and vinylacetate, polyvinyl alcohol, cellulose esters, cellulose ethers, and polyethylene glycol. Exemplary starches which may be used in the present invention are native or modified starches derived from corn, wheat, rice, potato, tapioca, or high amylose starch. Sources of starch which may be used also include flours from grains such as corn, wheat, durum wheat, rice, barley, oat, or rye, and mixtures thereof.

Additional matrix components which may be used include carbohydrates which have a lower molecular weight than starches. The lower molecular weight matrix components tend to dissolve more readily than does the starch and increase the penetrability or porosity of the matrix. As a result, access by the dissolution medium, such as water or acid, to the encapsulant is increased thereby permitting quicker release of the encapsulant from the matrix material. Examples of carbohydrates other than starch which may be used are sugars, such as mono- and di-saccharides, and starch hydrolyzate products such as dextrins or syrups with dextrose equivalent values (DE values) ranging from about 2 to about 99, or from about 5 to 98, and mixtures thereof.

The matrix material is used in an effective encapsulating amount. In embodiments of the present invention, the matrix material content, such as the starch content of the particles may be at least about 40% by weight, for example from about 60% by weight to about 95% by weight, based upon the weight of the final product.

The plasticizer or softener which may be used to lower the melt temperature or glass transition temperature ($T_g$) of the matrix material and facilitate plastification is preferably water but may be an aqueous-based composition such as a sugar solution, alcohol, sorbitol, polyethylene glycol, polypropylene glycol, silicone, hexanol, pentanol, dimethylsulfoxide (DMSO), hexane, or an oil. The amount of plasticizer, such as water, should be sufficient to substantially reduce the melt or glass transition temperature of the plasticizable material such as starch so that it may be admixed with the other ingredients at a sufficiently low temperature and under sufficiently low shear conditions so as to avoid substantial mechanical or thermal destruction of the plasticizable material or matrix material. Exemplary amounts of plasticizer, such as water, may range from about 20% by weight to about 50% by weight, preferably from about 35% by weight to about 45% by weight, most preferably about 40% by weight based upon the weight of the plasticizable material or matrix material such as starch.

The additional ingredients which may be used to control the release properties of the final product may be a hydrophobic agent for slowing down the rate of release of the encapsulant. Exemplary of components which may be added to affect the hydrophobicity of the matrix include fats, oils, waxes, fatty acids, emulsifiers, such as mono- or di-glycerides, synthetic polymers such as polyolefins such as polyethylene or polypropylene, polyvinyl chloride, polyvinyl acetate and derivatives thereof, paraffin, and modified starches from plant sources that possess hydrophobic properties that are obtained via either physical or chemical modification, and mixtures of hydrophobic components. Plant lipids or synthetic lipids with melting points up to about 65° C. may, for example, be employed as a hydrophobic agent. The hydrophobic components increase the hydrophobicity of the matrix and help to prevent or delay penetration of water or gastric juice into the matrix by repelling water or aqueous acids, thereby delaying the release of the encapsulant into the surrounding media.

Additional components which may be used to delay or prevent a fast release of the encapsulant from the matrix are components or agents which have a high water binding capacity. The agents may have a water binding capacity or water holding capacity which is greater than the water binding capacity of the matrix material, such as starch. The high water binding capacity component may bind water which penetrates the particles, or prevent the water from dissolving the matrix, thereby preventing or delaying the release of the encapsulant from the matrix. Exemplary of high water binding capacity agents which may be used in the present invention are protein from animal sources such as gelatin, casein, and protein from sources such as wheat, soy, corn, or other grains, and hydrocolloids such as carrageenans, alginates, xanthan gum, gum arabic, guar flour or guar gum, agar, tragacanth, karaya, locust bean gum, pectin, soluble fiber, insoluble fiber and the like. Exemplary proteins from grains which may be used are gluten, vital wheat gluten, zein, and soy protein concentrate. The proteins from plant sources may also be used to increase the tolerable addition of lipids within the matrix composition and thereby indirectly increase the hydrophobicity of the matrix. The high water binding capacity components may be used alone or mixtures thereof may be employed.

The additional components or ingredients used to control the rate of release of the encapsulant may be used in amounts up to about 70% by weight, preferably from about 5% by weight to about 50% by weight, most preferably from about 10% by weight to about 35% by weight, based upon the weight of the matrix material, such as starch.

Active components which may be encapsulated or embedded in the matrixes in accordance with the present invention include pharmaceutical compositions or compounds, nutraceutical compositions or compounds, nutritional components, or biologically active components, flavorants, fragrances, detergents or surface-active compositions. The pharmaceutical compounds or compositions may, for example, include antibiotics, analgesics, vaccines, antiinflammatory agents, antidepressants, anti-viral agents, anti-tumor agents, enzyme inhibitors, formations containing zidovudine, macromolecular polypeptides, aromatic nitro and nitroso compounds and their metabolites useful as antiviral and anti-tumor agents, HIV protease inhibitors, viruses, and steroids, mixtures thereof, and the like.

Nutraceutical components may include components which promote health or prevent disease or enhance well-being such as antioxidants, phytochemicals, hormones, vitamins such as Vitamin C and Vitamin E, pro-vitamins, minerals, microorganisms such as bacteria, fungi, and yeast, prebiotics, probiotics, trace elements, essential and/or highly unsaturated fatty acids such as omega-3 fatty acids, and mid-chain triglycerides, nutritional supplements, enzymes, pigments, oligopeptides, dipeptides, and amino acids.

Biologically active components which may be encapsulated include agriculturally useful compositions to either prevent infestation such as herbicides, pesticides, insecticides, rodenticides, fungicides, mixtures thereof, and the like or to promote growth such as hormones, fertilizers, or other growth stimulating agents.

Exemplary of the active components which may be encapsulated or embedded in accordance with the present invention are: acepromazine, acetaminophen, acetohexamide, acetohydroxamic acid, acetylcholine, acetylcysteine acyclovir, albendazole, alclometasone dipropionate, allopurinol, alprazolam, alprostadil, amcinoide, amantadine, amdinocillin, amikacin amiloride, aminocaproic acid, aminophylline, aminosalicylate, aminosalicylic acid, amitriptyline hydrochloride, ammonium chloride, amobarbital, amodiaquine hydrochloride, amoxapine, amoxicillin, amphetamine sulfate, amphotericin, ampicillin amprolium, acetazolamide acetyldigoxin, acetylsalicylic acid, anileridine, anthralin, antipyrine, antivenin, apomorphine, apraclonidine, ascorbic acid, aspirin, acromycin atropine, amoxycillin anipamil, azaperone azatadine maleate, azathioprine, azithromycin, aztreonam, bacampicillin, bacitracin, baclofen, barium salts, beclomethansone dipropionate, belladonna extract, bendroflumethiazide, benoxinate hydrochloride, benzethonium chloride, benzocaine, benzonatate benzthiazide, benztropine mesylate, betaine, betamethasone, betaxolol, betanechol chloride, biotin, biperiden, bisacodyl, bismuth, botulism antitoxin, bromocriptine mesylate, bromodiphenhydramine hydrochloride, bumetanide, bupivacaine, busulfan butabarbital sodium, butalbital, combinations of butalbital, caffeine and aspirin and codeine, beta-carotene, calcifediol, calcium carbonate, calcium citrate, calcium salts, candicidin, captopril, carbachol, carbamazepine, carbenicillin indanyl sodium, carbidopa, carbinoxamine maleate, carboprost tromethamine, carboxymethyl cellulose, carisoprodol, casanthranol, cascara, castor oil, cefaclor, cefadroxil, cefamandole nafate, cefazolin, cefixime, cefoperazone, cefotaxime, cefprozil, ceftazidime, cefuroxime axetil, cephalexin, cephradine, chlorambucil, chloramphenicol, chlordiazepoxide, chloroquine phosphate, chlormadinone acetate, chlorothiazide, chlorpheniramine maleate, chloroxylenol, chlorpromazin, chlorpropamide, chlorprothixene, chlorprothixene, chlortetracycline bisulfate, chlortetracycline hydrochloride, chlorthalidone, chlorzoxazone, cholecalciferol, cholera vaccine, chromic chloride, chymotrypsin, cimetidine, cinoxazin, cinoxate, ciprofloxacin, cisplatin, clarithromycin, clavulanate potassium, clemastine fumarate, clidinium bromide, clindamycin hydrochloride, -palmitate and -phosphate, clioquinol, clofazimine, clofibrate, clomiphene citrate, clonazepam, cinnarizine, clonidine hydrochloride, clorsulon, clotrimazole, cloxacillin sodium, cyanocobalamin, cocaine, coccidioidin, cod liver oil, codeine, colchicine, colestipol, corticotropin, corisone acetate, cyclacillin, cyclizine hydrochloride, cyclobenzaprine hydrochloride, cycloposphamide, cycloserine, cyclosporine, cyproheptadine hydrochloride, cysteine hydrochloride, danazol, dapsone, dehydrocholic acid, demeclocycline, desipramine, desoximetasone, desoxycorticosterone acetate, dexamethasone, dexchlorpheniramine maleate, dexpanthenol, dextroamphetamine, dextromethorphan, diazepam, diazoxide, dibucaine, dichlorphenamide, dicloxacillin sodium, dicyclomine, dienestrol, diethylpropion hydrochlorid, diethylstilbestrol, diflunisal, digitalis, dicoumarol, digitoxin, digoxin, dihydroergotamine, dihydrostreptomycin, dihydrotachysterol, dihydroxyaluminium amino acetate, dihydroxyaluminium sodium carbonate, diltiazem hydrochloride, dimenhydrinate, dimercaprol, diphenhydramine hydrochloride, diphenoxylate hydrochloride, diphteria antitoxin, dipyridamole, disopyramide phosphate, disulfiram, dobutamine hydrochloride, docusate calcium, docusate sodium, dopamine hydrochloride, doxepin hydrochloride, doxycycline, doxycycline hyclate, doxylamine cuccinate, dronabinol, droperidol, drotaverine, dydrogesterone, dyphylline, guaifenesin, enalapril maleate, analaprilat, ephedrine epinephrine, equilin, ergocalciferol, ergoloid mesylates, ergonovine maleate, ergotamine tartrate, erythrityl tetranitrate, erythromycin, estradiol, estriol, estrogene, estrone, estropipate, ethcrynic acid, ethambutol hydrochloride, ethchlorvynol, ethinyl estradiol, ethionamide, ethopropazine hydrochloride, ethotoin, ethynodiol diacetate, etidronate disodium, etoposide, eugenol, famotidine, fenoprofen, ferrous fumatate, ferrous gluconate, ferrous sulfate, flucytosine, fludrocortisone acetate, flunisolide, fluocinolone acetonide, fluocinonide, fluorescein sodium, fluorometolone, fluorouracil, fluoxymesterone, fluphenazine, flurandrenolide, flurazpam, flurbiprofen, folic acid, furazolidone, flunitrazepam, furosemide, gemfibrozil, gentamicin, gentian violet, glutarate, glutethimide, glycopyrrolate, chorionic gonadotropin, gramicidin, griseofulvin, guaifenesin, guanabenz, guanadrelsulfate, halazone, haloperidol, haloprogin, halothane, heparin calcium, hepatitis virus vaccine, hetacillin potassium, hexylresorcinol, histamine phosphate, histidine, homatropine, histoplasmin, hydralazine hydrochloride, hydrochlorothiazide, hydrocodone bitartrate, hydrocortisone, hexobarbital, hydroflumethiazide, hydromorphone hydrochloride, hydroquinone, hydroxocobalamin, hydroxyamphetamine, hydroxychloroquine sulfate, hydroxyprogesterone caproate, hydroxyurea, hydroxine hydrochloride, hydroxine pamoate, hyoscyamine, hyoscyamine sulfate, ibuprofen, ifosfamide, imipramide, imipramide hydrochloride, indapamide, indomethacin, insulin, inulin, iocetamid, iodoquinol, iohexol, iopamidol, ipecac, ipodate calcium, ipodate sodium, isocarboxacid, isoetharine hydrochloride, isoflurane, isoniacid, isopropamide iodine, isoproterenol hydrochloride, isosorbide dinitrate, isotretenoin, isoxsuprine hydrochloride, kanamycin sulfate, ketoprofen, ketoconazole, labetalol hydrochloride, lanolin, leucine, leucovorin calcium, levamisole hydrochloride, levocarnithine, levodopa, levonorgestrel, levorphanol tartrate, levothyroxine sodium, lidocaine, lincomycin hydrochloride, lindane, liothyronine sodium, liotrix, lisinopril, lithium carbonate, loperamide hydrochloride, loracarbef, lonetil, lorazepam, lovastatin, loxapine, lysine, mafenide acetate, magaldrte, magnesium carbonate, magnesiumchloride, magnesium gluconate, magnesium oxide, other magnesium salts, malathinon, manganese salts, manganese, maprotiline hydrochloride, mazindol, measle virus vaccine, mebendazole, mebrofenin, mecamylamine hydrochloride, meclizine hydrochloride, meclocycline, meclofenamate sodium, medroxyprogesterone acetate, mefenamic acid, megestrol acetate, meglumine, melphalan, menadiol sodium diphosphate, menadione, menotropine, meperidine, mephenytoin, mephobarbital, meprednisone, meprobamate, mercaptopurine, mesoridazine besylate, mestranol, metaproterenol sulfate, metaraminol bitartrate, methacycline hydrochloride, methadone hydrochloride, methamphetamine hydrochloride, methazolamide, methdilazine, methenamine, methicillin sodium, methimazole, methionine, methocarbamol, methotrexate, methoxsalen, methoxyflurane, methsuximide, methyclothiazide, methylbenzethonium chloride, methyldopa, methylergonovine maleate, methylphenidate hydrochloride, methylprednisolone, methyltestosterone, methysergide maleate, metoclopramide, metolazone, meoprolol tartrate, metronidazole, metyrapone, metyrosine, mexiletine hydrochloride, mexiletine hydrochloride, miconazole, minocycline hydrochloride, minoxidil, mitomycin, mitotane, molindone hydrochloride, monobenzone, morphine sulfate, mupirocin, medazepam, mefruside, methandrostenolone, methylsulfadiazine, nadolol, nafcillin, nafcillin sodium, nalidixic acid, nalorphine, naloxone, nandrolone decanoate, nandrolone phenpropionate, naproxen, natamycin, neomycin, neomycin sulfate, neostimine bromide, niacin, nitrofurantoin, nalidixic acid, nifedipine, nitrazepam, nitrofurantoin, nitroglycerine, nitromerson, nizatidine, nonoxynol 9, norethindrone, norethindrone acetate, norfloxacin, norgestrel, nortriptyline hydrochloride, noscapine, novobiocin sodium, nystatin, opium, oxacillin sodium, oxamniquine, oxandrolone, oxazepam, oxprenolol hydrochloride, oxytriphylline, oxybenzone, oxybutynin chloride, oxycodone hydrochloride, oxycodone, oxymetazoline hydrochloride, oxymetholone, oxymorphone hydrochloride, oxyphenbutazone, oxytetracycline, padimate, panreatin, pancrelipase, papain, panthenol, papaverin hydrochloride, parachlorophenol, paramethasone acetate, paregoric, paromomycin sulfate, penicillamine, penicillin, penicillin derivatives, pentaerythritol tetranitrate, pentazocine, pentazocine hydrochloride, pentazocine salts, pentobarbital sodium, perphenazine, pertussis, phenacemide, phenazopyridine hydrochloride, phendimetrazine tartrate, phenelzine sulfate, phenmetrazine hydrochloride, phenobarbital, phenophtalein, phenoxybenzamine hydrochloride, phentermine hydrochloride, phenylalanine, phenylbutazone, phenylephrine hydrochloride, phenylpropanolamine hydrochloride, physostigmine, phytonadione, pilocarpine, pimozide, pindolol, piperazine, piroxicam plicamycin, poliovirus vaccine inactivated, polycarbophil, polymycin b sulfate, polythiazide, potassium chloride, potassium citrate, potassium cluconate, potassium iodine, potassium sodium tartrate, povidone iodine, pralidoxime chloride, pramoxine hydrochloride, pramezam, prazepam, praziquantel, prazosin hydrochloride, prazosin hydrochloride, prednisolone, prilocaine, primaquine, primidone, probenecid, probucol, procainamide hydrochlorid, procaine hydrochloride, procarbacine hydrochloride, prochlorperazine, prochlorperazine maleate, procyclidine hydrochloride, progesterone, proline, promazine, promazine hydrochloride, promazine, promethazine, promethazine hydrochloride, propafenone hydrochloride, propantheline, proparacaine hydrochloride, propoxycaine hydrochloride, propoxyphene hydrochloride, propoxyphene napsylate, propanolol hydrochloride, propyliodone, propylthiouracil, propylthiouracil, protriptyline hydrochloride, pseudoephedrine hydrochloride, pumice, pyrantel pamoate, pyrazinamide, pyrethrum extract, pyridostigmine bromide, pyridoxine hydrochloride, pyrilamine maleate, pyrimethamine, pyroxylin, pyrvinium pamoate, phenacetin, phenytoin, prednisone, uinidine gluconate, quinidine sulfate, rabies vaccine, racepinephrine ranitidine, rauwolfia serpentina, resorcinol, ribavirin, riboflavin, rifampin, ritodrine, rubella virus vaccine, saccharin, saccharin sodium, salicylamide, salicylic acid, salsalata, scopolamine, secobarbital sodium, selenius acid, selenium sulfate, sennaserine, simethicone, sodium ascorbate, sodium bicarbonate, sodium fluoride, sodium gluconate, sodium iodide, sodium lactate, sodium nitrite, sodium ditroprusside, sodium salicylate, spironolactone, stannozolol, streptomycin, sucralfate, sulfacetamide, sulfadiazine, reserpine, sulfadioxine, sulfamerazine, sulfamethazine, sulfamethizole, sulfamethoxazole, sulfamethoxydiazine, sulfapyridin, sulfasalazine, sulfaperin, sulfathiazole, sulfisoxazole, sulfinpyrazone, sulindac, suprofen, stilains, tamoxifen citrate, temacepam, terbutaline sulfate, terfenadine, terpin, testolacton, testosterone, tolazamide, tolbutamide, tetracaine, tetracycline, tetrahydrocycline, theophylline, thiabendazole, thiamine hydrochloride, thiamin, thiamylal, thiethylperazine thimerosal, thioguanine, thioridazine hydrochloride, thistrepton, thiotepa, thiothixene, threonine, thyroid, ticarcillin, timolol, tioconazole, titaniumdioxide, tolazamide, tolbutamide, tolmetin, tolnaftate, trazodone hydrochloride, tretinoin, triacetin, triamcinolone, triamterene, triazolam, trichorfon, trichlormethiazide, trientine hydrochloride, trifluoperazine hydrochloride, triflupromazine, trihexyphenidyl hydrochloride, trimeprazine tartrate, trimethadione, trimethobenzamide hydrochloride, trimethoprim, trioxsalen, tripelennamine, triprolidine, trisulfapyrimidine, tropicamide, trypsin, tryptohan, tuberculin, tyloxapol, tyropanoate sodium, tyrosine, tyrothricin, thyrothricin bethamethasone, thiotic acid, sotalol, salbutamol, norfenefrine, silymarin, dihydroergotamine, buflomedil, etofibrate, indometacin, urea, valine, valproic acid, vancomycin hydrochloride, vasopressin, verapramil, vidarabine, vinblastine, vincristine, vitamins, warfarin, yellow fever vaccine, zinc acetate, zinc carbonate, zinc chloride, zinc gluconate, beta acetyl digoxin, piroxicam, haloperidol, ISMN, amitriptyline, diclofenac, nifedipine, verapamil, pyritinol, nitrendipin, doxycycline, bromhexine, methylprdnisolone, clonidine, fenofibrate, allopurinol, pirenyepine, levothyroxin, tamoxifen, metildigoxin, o-(beta-hydroxyethyl)-rutoside, propicillin, aciclovir mononitrate, paracetamol, naftidrofuryl, pentoxifylline, propafenone, acebutolol, L-thyroxin, tramadol, bromocriptine, loperamide, ketotifen, fenoterol, cadobelisate, propanolol, enalaprilhydrogen maleate, bezafebrate, ISDN, gallopamil, xantinol nicotinate, digitoxin, flunitrazepam, bencyclane, dexapanthenol, pindolol, lorazepam, diltiazem, piracetam, phenoxymethylpenicillin, furoseinide, bromazepam, flunarizin, erythromycin, metoclopramide, acemetacin, ranitidin, biperiden, metamizole, doxepin, dipotassium chloroazepate, tetrazepam, estramustine phosphate, terbutaline, captopril, maprotiline, prazosin, atenolol, glibenclamide, cefaclor, etilfrine, cimetidine, theophylline, hydromorphone, ibuprofen, primidone, clobazam, oxaceprol, medroxyprogesterone, flecainid, pyridoxal 5 phosphate glutaminate, hymechromone, etofylline clofibrate, vincamine, cinnarizine, diazepam, ketoprofen, flupentixol, molsimine, glibornuride, dimetinden, melperone, soquinolol, dihydrocodeine, clomethiazole, clemastine, glisoxepide, kallidinogenase, oxyfedrine, baclofen, carboxymethylcysteine, thioridazine, betahistine, L-tryptophan, murtol, bromelaine, prenylamine, salazosulfapyridine, astemizol, sulpiride, benzerazide, dibenzepine, acetylsalicylic acid, miconazol, nystatin, ketoconazole, sodium picosulfate, coltyramine, gemfibrocil, rifampicin, fluocortolone, mexiletin, amoxicillin, terfenadrin, mucopolysaccharide polysulfade, triazolam, mianserin, tiaprofenic acid, amezinium metilsulfate, mefloquine, probucol, quinidine, carbamazepine, L-aspartate, penbutolol, piretanide, aescin amitriptyline, cyproterone, sodium valproinate, mebeverine, bisacodyl, 5-aminosalicylic acid, dihydralazine, magaldrate, phenprocoumon, amantadine, naproxen, carteolol, famotidine, methyldopa, auranofine, estriol, nadolol, levomepromazine, doxorubicin, medofenoxate, azathioprine, flutamide, norfloxacin, fendiline, prajmalium bitartrate, lipid derivatives of phosphonatides, amphiphilic polymers, adenosine derivatives, sulfated tannins, monoclonal antibodies, and metal complexes of water soluble texathyrin.

The amount of the active component or encapsulant which is incorporated into the products of the present invention may be such so as to provide or deliver an effective amount, such as a pharmaceutically effective amount or a nutraceutically effective amount of the active component at its intended location, such as the small intestine. Exemplary amounts of the active component or encapsulant which may be encapsulated or embedded into the matrix may be from about 1% by weight to about 85% by weight, preferably from about 3% by weight to about 50% by weight, based upon the weight of the matrix ingredient, such as starch.

Film-building or film-forming substances which may be used to coat the encapsulants prior to incorporation into the matrix include commonly used coating materials such as zein, pectin, shellac, gelatin, fats, oils, waxes, emulsifiers, native or modified starch, chitosan, chitin, and mixtures thereof. The film-building or film-forming substance may also be used to coat the extruded, particulate product. Pretreatment of the encapsulant by coating it with a film forming substance such as a high melting fat or wax, or with an emulsifier such as glycerin monostearate, or the like, tends to prevent unwanted interaction between an encapsulant and the matrix. The encapsulants and the extrudate particles may be coated with film-forming amounts of the substances in aqueous or alcoholic solutions, or oleaginous compositions.

The film-forming substances or coatings may also contain additional components that protect the particulates or pellets, or encapsulant, from the influence of light, such as titanium dioxide, or cocoa-based products. The coatings may also contain anti-oxidants to protect the pellets or encapsulants from the influence of oxygen or air.

In accordance with embodiments of the present invention, the thickness of the coating upon the encapsulant may be used to control the rate of release of encapsulant once the dissolving media, such as water, reaches the encapsulant. For example, increasing the thickness of the coating on the encapsulant slows its rate of release into the media. Also, increasing the thickness of the coating on the extrudate or pellet delays release of the encapsulant from the matrix material.

In accordance with the method of the present invention, the matrix material or plasticizable material and the plasticizer are admixed and heated to plasticize and melt the matrix material under low shear mixing conditions without substantially destroying or decomposing the matrix material. In preferred embodiments, the matrix material and the plasticizer may be added to the upstream end of an extruder, mixed and heated above the melt temperature of the plasticizable material or above the gelatinization temperature of starch while mixing and conveying these ingredients inside the extruder. In embodiments where starch is used as a matrix material, the starch is at least partially gelatinized without substantially destructurizing and dextrinizing the starch. The degree of gelatinization may, for example, be at least about 75%, for example, at least about 90%, or essentially completely gelatinized. In embodiments of the invention, to achieve at least substantial gelatinization of starch, the starch and plasticizer (preferably water) admixture may be maintained at a temperature of the blend of at least about 100° C., preferably from about 120° C. to about 150° C., for example, from about 125° C. to about 140° C., for a period of time of at least about 3 l/d preferably about 5 to 7 l/d of extruder length. For example, for starches having an amylose content of more than about 25%, for example about 50% to about 70%, it may be necessary to maintain a product temperature inside the extruder of about 125° C. for a sufficient amount of time, for example for about 4 l/d, preferably about 7 to 8 l/d of extruder length at a low screw rotational rate of about 150 to about 200 rpm using medium pitch screw elements to assure at least substantial gelatinization of the starch.

In embodiments of the invention, the pressure maintained within the cooking section or gelatinization section or plastification zone may be between about 5 to 100 bars, preferably between about 10 and 35 bars.

An overall quantitative measure of the shear used inside the extruder during the cooking process is the specific mechanical energy input. In embodiments of the present invention, the specific mechanical input during cooking may be below about 150 Wh/kg, preferably below about 100 Wh/kg, and most preferably below about 50 Wh/kg.

In embodiments where durum wheat is used as the matrix material, heating of the durum wheat and water mix to cook or gelatinize the durum wheat may not be needed where an uncooked pasta-type product is desired.

The at least one additional ingredient or component, such as the hydrophobic component, or high water binding capacity component for controlling the release properties of the final product, may be dry blended or preblended with the matrix material such as starch. In other embodiments of the invention, the additional component for controlling the release properties may be added during heating in a heating or gelatinization zone. Addition of the at least one release-controlling component prior to substantial water evaporation or cooling may also facilitate at least substantially uniform dispersion of the component throughout the matrix.

The plasticized mass may be subjected to moisture reduction during heating or gelatinization, downstream of the input of the release-controlling components. In embodiments of the invention, the water content may be substantially reduced so as to facilitate forming and enable optional cutting without the material sticking to the cutter. For example, the water content may be reduced by at least about 10%, for example by about 25% to about 50%. For example, a plasticized starch matrix having an initial moisture content of about 43% by weight may have its moisture content reduced to about 30% by weight. In other embodiments, a gelatinized starch composition may have its moisture content reduced from about 30% by weight to about 18% by weight.

The removal of water may be achieved by passing the at least partially plasticized or gelatinized mixture through an extruder barrel section that is open to the atmosphere. In other embodiments, the moisture may be removed by reducing the pressure above the material while it moves underneath an open extruder section or barrel that is connected to an external vacuum pump. A plurality of open extruder barrel sections in series may also be used. The plurality of open barrel sections may be open to the atmosphere or connected to one or more vacuum pumps or combinations thereof may be used. In another embodiment, the material may be transferred from a first cooking extruder into a downstream or subsequent mixing and forming device such as an extruder. During the transfer, the material may be permitted to undergo a temperature and moisture drop by exposure to the atmosphere or a vacuum hood.

After heating and moisture content reduction, the plasticized or gelatinized mass may be subjected to cooling to substantially reduce the temperature of the mass for the subsequent addition of the active component or encapsulant. In embodiments of the invention, the temperature of the matrix material is substantially reduced to avoid substantial destruction of the encapsulant. The matrix material temperature may, for example, be reduced by at least 5° C., generally at least about 25° C., preferably at least about 60° C. In embodiments of the invention, the temperature of the matrix material may be cooled to substantially lower than 100° C., for example, to a temperature of between about 25° C. and 95° C., in one or more extruder barrels. The material may be transported through and exposed to the barrel walls of one or more extruder barrels that are chilled with water or appropriate other cooling liquids such as a glycol. In other embodiments of the invention, the matrix material may be cooled or chilled by the direct injection of gases such as carbon dioxide or nitrogen which reduce the temperature of the matrix material by direct contact. The matrix material, after moisture reduction and temperature reduction, may be conveyed toward a subsequent extruder barrel section for the addition of one or more active components.

After cooling the matrix material to a temperature which is sufficiently low to avoid substantial thermal destruction and/or volatilization of the active component or encapsulant, the encapsulant may be added into a downstream barrel section of the extruder. The added active component or encapsulant may be added as a solid or liquid. For feeding the active components to an extruder, for example, a feeding apparatus, commonly known as a side feeder, may be used for feeding solids. Other conventional solids feeding devices such as a volumetric or gravimetric feeder may also be used. Liquid injection nozzles may be used for injecting liquid active components or solutions, dispersions, emulsions or suspensions. In embodiments of the invention, a side feeder and liquid injection nozzles may be employed. If an injection nozzle is used, the pressure for injecting the liquid encapsulant should be sufficiently higher than the pressure in the extruder so that the encapsulant can be injected into the extruder barrel. For example, if the pressure of the plasticized mass inside the extruder is 10 bars, the injection pressure may be about 2 to about 5 bars higher, i.e. 12 to 15 bars.

In embodiments where the encapsulant is pre-coated with a film-building material or coating material, the coating material may be applied in conventional manner such as by spraying or enrobing using conventional coating equipment. Commercially available pre-coated active ingredients, such as precoated minerals or vitamins may be employed.

The encapsulant which itself may be optionally coated, is admixed with the matrix material without substantially destroying the encapsulant or the precoated encapsulant. The mixing may be conducted at a temperature which is substantially lower than the degradation temperature of the encapsulant and its optional precoating. For example, admixing of the encapsulant with the matrix material may be performed at a temperature substantially less than about 100° C., preferably at a temperature less than about 60° C., most preferably less than about 40° C.

The admixing of the added active ingredients or encapsulants inside the extruder may be accomplished by using an appropriate extrusion screw configuration for achieving low shear mixing. For example, a combination of alternating small pitch conveying elements with distributive mixing elements, that are staggered at an angle to each other for providing axially oriented leakage flow inside the extruder barrel may be employed. The combination of alternating conveying elements with distributive mixing elements cause the material flow to be continuously interrupted without shearing of the mass thus resulting in mixing of the material at low mechanical energy input.

In other embodiments of the invention, other extruder screw configurations may be used that facilitate low shear distributive mixing, such as screw elements of the type ZME, TME, SME, and so-called IGEL elements commercially available from Werner and Pfleiderer.

The total length of the distributive mixing section may be about 3 to 12 l/d, preferably about 4 to 6 l/d to sufficiently admix and distribute and embed or encapsulate the added active components in the matrix.

The at least substantially homogeneous mixture of matrix material and added active ingredient or encapsulant is then conveyed towards an extruder die plate. The conveying may be achieved by the use of low pitch extruder screw conveying elements which build up sufficient pressure prior to extruding the mix so that it can be forced through the apertures in the die plate. Another function of the low pitch elements is that they increase the degree of fill inside the last extruder barrel section. The increased degree of fill enables control of the temperature profile of the mix inside the extruder barrel for achieving optimum viscosity adjustment and extrusion through the subsequent die openings.

The mix may be extruded through extrusion dies having aperture diameters of from about 0.5 mm to about 5 mm, preferably from about 0.5 mm to about 1 mm. The diameter of the extrudate rope and product may be larger than the diameter of the die apertures due to deformation or swelling as the composition exits the die. The increase in diameter upon exiting the die may occur without substantial development of an expanded, puffed, foamy, or cellular structure. The extruded rope may have a cross-sectional diameter of from about 0.5 mm to about 7 mm, preferably from about 0.5 mm to about 5 mm, most preferably from about 1 mm to about 3 mm.

The extrudate rope may be cut at the die face using a rotating cutter, pelletizer, or rotating knives. In other embodiments, the extrudate rope may be cut away from the die using conventional cutting or forming means for producing pellets or tablets. The cut pieces, pellets, or tablets, may have a length:diameter ratio (l/d ratio) of about 0.5 to 10, preferably about 1.

In accordance with the process of the present invention, the particle size may be varied to control the surface to volume ratio of the pellets or pieces for achieving a desired controlled release of the encapsulant. The particle size may be varied, for example, by the use of different diameters for the extrusion die openings. Particle size may also be varied by the use of a variable speed cutter either at the die plate at the end of the extruder or away from the extruder after the ropes have been conveyed for a short distance. By varying the speed of the cutter, the size of the cut pieces may be varied for a given extruder throughput. The use of a variable cutter which is spaced a short distance from the die plate, for example, between about 0.5 meters to about 5 meters permits further surface cooling, further surface drying, and reduced stickiness to provide better cutting of the ropes into pellets.

In producing products for human or animal consumption, variation of particle size to control the surface to volume ratio of the pellets is critical for achieving a controlled release of the encapsulant during passage of the pellets or particles through the mouth, the stomach, and the intestine. Variation of particle size is also critical for controlling the residence time of the pellets inside the stomach. For example, particles smaller than 1 mm pass through the stomach or intestine faster than would particles larger than for example 2.5 mm.

After cutting, the resulting pieces or pellets may be dried to a sufficiently low moisture content which assures a sufficiently prolonged storage stability or shelf life. For example, the pellets may be dried to achieve a storage stability or shelf life of at least about nine months, preferably at least about eighteen months, most preferably at least about thirty-six months. In embodiments of the present invention, the drying may be performed using conventional drying equipment using drying temperatures which do not adversely affect the thermal stability of the encapsulants. Exemplary drying temperatures may range from about 10° C. to about 90° C., preferably from about 20° C. to about 60° C. The drying may be conducted to achieve a moisture content of less than about 30% by weight, preferably less than about 12% by weight, for example, from about 6% by weight to about 9% by weight. In embodiments where no starch or substantially no starch is used as a matrix material, the moisture content may be less than about 6% by weight.

In embodiments where film-building substances or coatings are applied to the particles or pellets, conventional spray nozzles may be located close to the die or for spraying an aqueous or alcoholic solution of the film-building substances onto the cut pieces as they fall downwardly from the extruder die. In other embodiments, the film-building substances may be applied after drying of the pellets. For example, the film-building substances may be applied using spray nozzles, conventionally known fluid bed coating apparatus, or other conventional coating apparatus and methods. If the application of the film-building substances increases the moisture content above a shelf stable level, the water or other volatile media may be removed from the surface of the particles by additional drying.

In embodiments of the present invention, the extruded pieces or pellets may be compressed in conventional tablet presses to obtain compressed versions of the extruded pellets.

In other embodiments of the present invention, the mixture may be extruded through a sheeting die into a sheet. The extruded sheet may then be cut or molded into individual pieces, such as tablets, or disks, using a rotary die or rotary cutter, or reciprocating cutter or counterrotating drums conventionally known as agglomeration drums or tabletting drums.

The products of the present invention comprise discrete particles which may be spherical, lens-shaped, or flat discs having diameters of from about 0.5 mm to about 7 mm, preferably from about 0.5 mm to about 5 mm, most preferably from about 1 mm to about 3 mm, exclusive of any optional exterior film-building substances or coatings. In embodiments of the invention, the particles of the invention may be in the form of tablets with diameters of up to about 10 mm. The length-to-diameter ratio (l/d) of the particles may be from about 0.1 to about 10, for example about 0.5 to about 2, preferably about 1. The particles are generally uniform in size, dense, and granular to increase palatability to humans and animals in a substantially compact form that is easy to swallow without chewing. They are non-expanded, and exhibit a non-puffed, substantially non-cellular, dense structure. The starch component of the matrices is at least partially gelatinized and not substantially destructurized or dextrinized. Exemplary specific densities of the products of the present invention are between about 800 g/liter and about 1500 g/liter (about 0.8 to about 1.5 g/cm$^3$).

FIG. 1 shows a simplified schematic representation of the process of the invention using an extrudes. A preblend that contains at least one starch and one additional component is fed into the upstream end of the extruder. Water is added into the same or one of the next immediately following barrel sections of the extruder. Co-rotating intermeshing twin screw extruders, such as those available from Buhler, Switzerland, Clextral France, Werner and Pfleiderer Germany, APV England or Wenger USA, or a Co-Kneader, available from Buss, Switzerland are preferred, since they provide superior mixing action compared to other single screw extruders. The preblended matrix materials, plasticizer such as water, additional components or matrix material are mixed in the extruder and heated so that the starch is at least partially gelatinized. As shown in FIG. 1, the additional ingredients for controlling release properties may be fed into the extruder and mixed with the matrix material before and/or after heating and plasticization of the starch. The total mix may be plasticized and pressurized using appropriate screw elements arranged in an appropriate matter.

After pressurizing and melting, the mass may be exposed to a lower pressure and at least part of the moisture may be removed from the matrix material. As illustrated in FIG. 1, in a subsequent step the mass may be cooled in one or more subsequent extruder barrels. After cooling of the mass, the optionally coated encapsulant material may be added at a low temperature, i.e. room temperature, so as to prevent thermal destruction of the encapsulant. The added encapsulant may be mixed at low shear and low temperature with the cooled, plasticized, matrix material. The final plasticized mass may be mixed, conveyed and forced through the extruder die. The mass may be formed into shapes that exit the extruder as continuous ropes. The ropes may be sprayed with liquids, that provide an additional coating or facilitate cutting to separate the individual pieces from each other. In embodiments of the invention, it is possible to perform the forming step using a single screw extruder.

As shown in FIG. 1, after cutting, the product may be dried using a conventional fluidized bed or other conventional drying means. The product may be optionally coated after drying using conventional coating equipment such as coating pans, coating drums, or spray devices.

Figure 2:
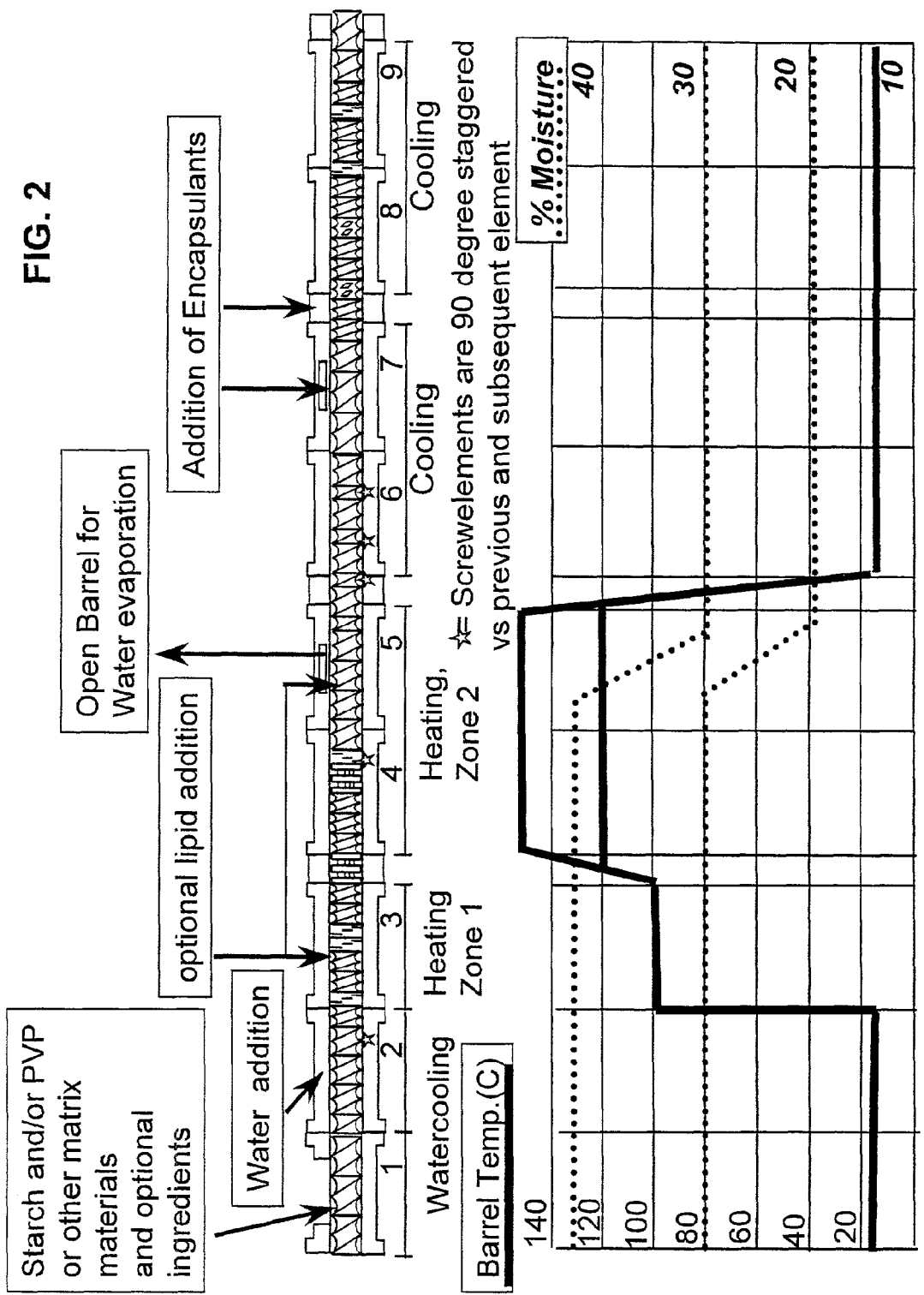
FIG. 2 is a schematic overview of the extrusion process of the present invention showing the screw configuration and barrel temperature profile for the extruder.

FIG. 2 shows schematically an overview of an extrusion process, an exemplary extruder barrel configuration, and screw configuration, in accordance with the present invention. Exemplary barrel temperatures or temperature profiles, and moisture contents along the length of the extruder are also shown in FIG. 2. A preblend of starches or other plasticizable material such as PVP or other matrix materials, with at least one more other component may be prepared and stored or conditioned prior to feeding it into the extruder. The dry blend is fed either gravimetrically or volumetrically into the feeding section of the extruder in barrel 1. Temperatures at this barrel section are normally about room temperature and can vary from about 0° C. to about 85° C. Higher temperatures tend to cause steam to escape from the feed port. Barrel (1) may be cooled with water to maintain a temperature between about 10° C. and 50° C. Screw elements with large pitch convey the dry blend into barrel 2. Elements with less pitch than in Barrel 1 increases the degree of fill in barrel 2. Offset forward pitch elements and small disk kneading blocks cause distributive mixing of the added liquid that may be added in barrels 1 and 2 with the dry blend. Simultaneously, the temperatures of barrel 2 and 3 may be elevated to about between 60 and about 150° C. to heat the wet blend, that is conveyed using medium pitch screw elements into barrel 4. The barrel temperature in barrels 4 and 5 may be between about 110° C. and 180° C., preferably between about 120° C. and 160° C. The temperature of the mix increases at a rate that is mainly affected by the contact time of the material and the barrel and exchange of material by the screws. The contact time is a function of rpm and throughput rate, which determine the degree of fill. The material exchange is affected by the screw configuration.

In barrel 4, mixing elements alternate with medium pitch conveying elements and ensure sufficient material exchange and a high degree of fill. Staggering kneading disks at an angle of 90 degrees to each other allows additional leakage flow and prevents high shear. As long as the energy dissipation into the material is low, which is the case at a relative low material viscosity, resulting from relatively high moisture contents, the mass is heated via the barrel wall and its temperature is normally a few degrees lower than the actual barrel temperature. The mass forms a dough, that may have a temperature of about 5° C. to 30° C. lower than the barrel temperature, in this case 90° C. to 155° C. With an extruder set up as described in FIG. 2, gelatinization of starch occurs within the first 4 barrel sections. Optional steam injection may be applied in this gelatinization or heating section to increase the thermal energy input and further decrease the mechanical energy input.

Before the vent opening in barrel 5, a kneading disc element increases the degree of fill and increases pressure of the mass in barrel 4. This pressure is needed to further enhance the cooking of the starch. If the starch is high in amylose, temperatures of about 120° C. may be reached under this pressure, which may be between about 5 and 30 bars, for example 10 bars. After this element, high pitch conveying elements follow, that decrease the degree of fill by their function of higher conveying capacity. One open barrel section 5, optionally connected to a vacuum pump, allows the pressure to decrease substantially, for example from about 10 bar to about less than 1 bar. This pressure drop results in water evaporation and subsequent moisture loss of the cooked mass. The amount of moisture evaporated to the atmosphere or to the vacuum, additionally depends upon the temperature of the product and residence time of the product in this open barrel section 5. Residence time is affected by the rpm of the screw, pitch of the screw elements, and available open area for water evaporation, which may vary from one, two or more vent ports. High barrel temperatures, above for example 150° C., force more steam to escape from the cooked mass than low barrel temperatures, for example 80° C. Exemplary temperatures in the vented heating zone of barrel 5 may be between about 80° C. and 160° C., preferably about 100° C. to 140° C.

The subsequent barrels 6 and 7 may be cooled down with water to reduce mass temperature further. Temperatures in this section may be between about 20° C. and 90° C. Low pitch conveying elements that are staggered increase degree of fill to enhance heat transfer from product to barrel in barrels 6 and 7. Low rpm are critical for optimum processing. Exemplary ranges which may be utilized are between about 20 and about 200 rpm. Higher rpm tend to introduce more shear, dextrinize and destructurize starch to a larger extent. Additionally higher screw speeds tend to severely reduce capability for water removal because the residence time in the open vent section is greatly reduced. Low screw speeds (rpm's) also increase the degree of fill and thus heat transfer capability, i.e. heating and cooling.

Barrel 7 may be open to the atmosphere to enable addition of encapsulant. Optionally, a side feeder (not shown) may be used that is directly connected to the side of the extruder to feed a solid encapsulant into the extruder. In addition, liquid encapsulants can be introduced into the blend via one or more injection nozzles into the same extruder barrel. The side feeder may be a conventional twin screw feeder. The temperature of the barrel is adjusted depending upon the heat sensitivity of the encapsulant and can, for example, be adjusted to temperatures between about 20 and 90 degree C.

The product temperature at the encapsulant input location in barrel 7 is sufficiently low so as to not thermally destroy or disintegrate the encapsulant. In case the encapsulant is oxygen sensitive, the hopper (not shown) of the side feeder (not shown) may be optionally flooded with $CO_2$ or nitrogen. After the mix has been introduced into the barrel section, it is conveyed into a barrel section 8 and then barrel section 9, both of which may contain screw elements with forward pitch and staggered position, that mix the added ingredients into the matrix while minimizing the introduction of shear energy. Simultaneously, the temperature of the barrels 8 and 9 may be maintained low enough so as to not thermally destroy the encapsulant and to ensure that the viscous properties of the dough are sufficiently high to allow extrusion and forming of ropes that can be cut into pellets. Temperatures may range between 25° C. and 95° C., preferably around 40° C. to 80° C.

After exiting the barrel section 9 of the extruder, the mass enters into the die area, where it is distributed into a multitude of openings. Critical is the rate of extrudate per die area, which should be less than about 5 kg/h per $mm^2$ preferably less than 3 kg/h per $mm^2$ and most preferably less than about 0.5 kg/h per $mm^2$. High rates will result in higher shear rates inside the die that will cause increased viscous dissipation, pressure and temperature which may adversely affect the encapsulant and may lead to unwanted product expansion.

Figure 3:
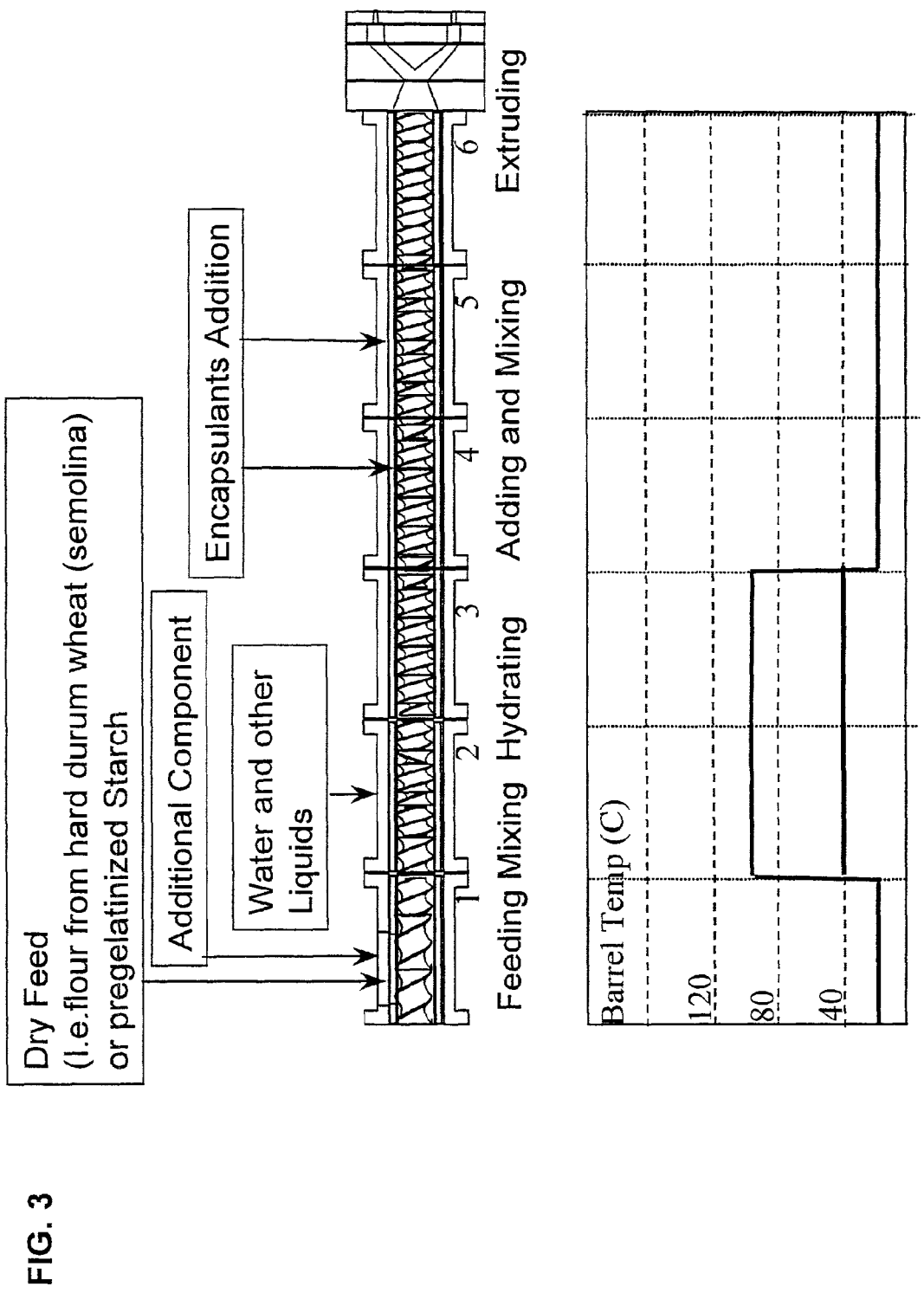
FIG. 3 shows an alternative process, extruder screw configuration and barrel temperature profile, where a pregelatinized starch or hard durum wheat is fed to the extruder using a relatively low temperature profile.

FIG. 3 shows an alternative execution of the invention, whereby the fed solid ingredients may be either pregelatinized starch or flour with specific properties, such as flour from durum wheat that is normally used to produce pasta, such as semolina. As shown in FIG. 3, the dry feed and at least one additional component for affecting the release properties may be fed to barrel 1 without cooking. The dry feed solids and the at least one more component to affect the release properties of the matrix may then be mixed with water in barrel 2 to hydrate the dry feed ingredients. In this case, the moisture needs to be sufficiently high so as to provide sufficiently low viscosity without destructurizing or dextrinizing the pregelatinized starch. For example, the added moisture content may be between about 20% and 45% by weight, preferably between about 25% and 35% by weight, for example about 30% by weight. As shown by the barrel temperature profile in FIG. 3, the temperature of the extruder barrel 1 is kept at about room temperature, but barrels 2 and 3 need to be about between 40° C. and 100° C. to maintain low viscosity and low specific mechanical energy input. The encapsulants may be added in barrel 4 and/or barrel 5 with continued mixing and conveying. The product may be cooled in barrels 4, 5, and 6 at the end of the extruder in similar manner as described for FIG. 2. Thus, the temperature of the barrels 4, 5, and 6 may be maintained low enough so as to not thermally destroy the encapsulant and to ensure that the viscous properties of the dough are sufficiently high to allow extrusion and forming of ropes that can be cut into pellets. Temperatures may range between 20° C. and 95° C. After exiting the barrel section 6 of the extruder, the mass enters into the die area, where it is distributed into a multitude of openings.

Figure 4:
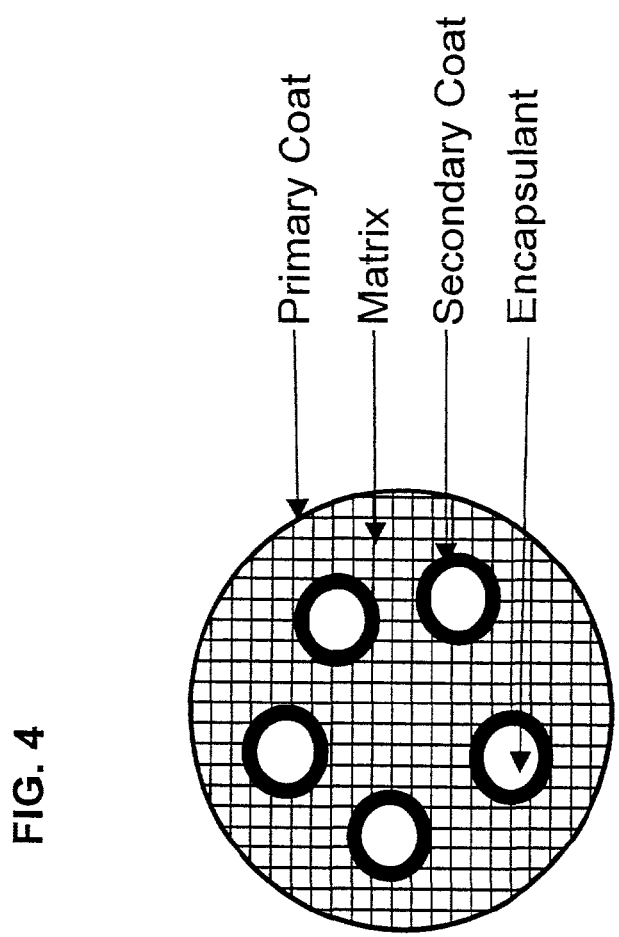
FIG. 4 shows a product in accordance with the present invention having a primary outer coating and an encapsulant which has a secondary coating.

FIG. 4 shows a spherical product which may be produced in accordance with the present invention. The pellet shown in FIG. 4 has a primary coating of a film-forming ingredient which enrobes or coats the underlying matrix material. An encapsulant, which has been pre-coated with a secondary coating of a film-forming ingredient, is encapsulated or surrounded by the matrix material. The primary coating and the secondary coating may be the same or different compositions.

Figure 5:
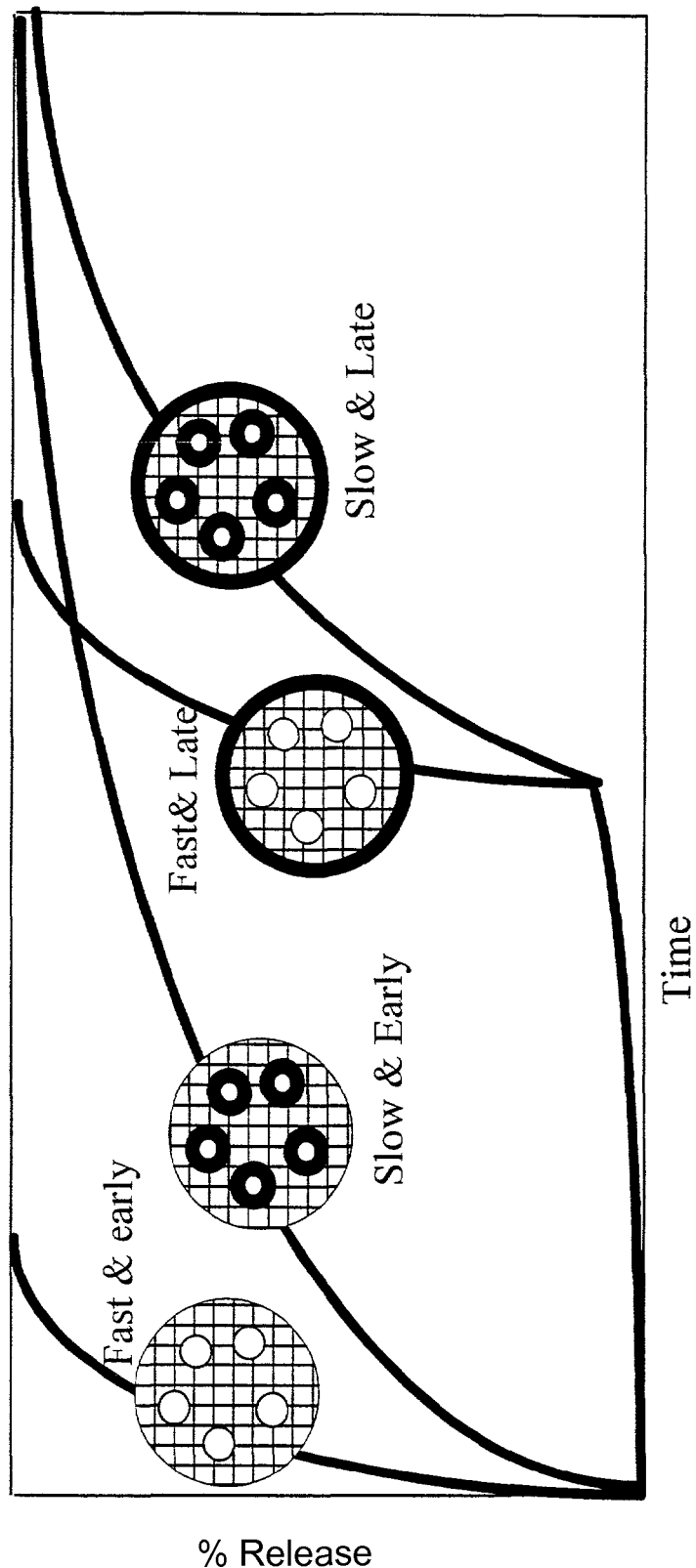
FIG. 5 shows four basic release properties of an encapsulant which is controllable by the use of optional coatings for the extrudate and encapsulant in accordance with the present invention.

FIG. 5 shows as an example of four basic release properties of the encapsulated products of the present invention which are dependent upon the presence and thickness and material of a coating for the discrete extrudate particles or for the encapsulant. According to the present invention, a primary factor that determines the release properties of the encapsulant from the matrix, is the matrix material, and particularly its diffusivity or solubility (against aqueous or digestive liquids). The diffusivity or solubility may be controlled by the hydrophobicity of at least one additional matrix component next to the starch. Also, as shown in FIG. 5, a fast and early release of encapsulant from the matrix may be achieved with a relatively thin primary coating and a relatively thin secondary coating. A slow but early release of encapsulant may be obtained with a relatively thin primary coating and relatively thick secondary coating. A fast but late release of encapsulant may be achieved with a relatively thick primary coating and a relatively thin secondary coating. A slow and late release may be achieved with a relatively thick primary coating and a relatively thick secondary coating.

The encapsulated products of the present invention may be incorporated with or without grinding into foods intended for human or animal consumption such as baked goods, for example, bread, wafers, cookies, crackers, pretzels, pizza, and rolls, ready-to-eat breakfast cereals, hot cereals, pasta products, snacks such as fruit snacks, salty snacks, grain snacks, and microwave popcorn, dairy products such as yoghurt, cheese, and ice cream, sweet goods such as hard candy, soft candy, and chocolate, beverages, animal feed, pet foods such as dog food and cat food, aqua-culture foods such as fish food and shrimp feed, and special purpose foods such as baby food, infant formulas, hospital food, medical food, sports food, performance food or nutritional bars, or fortified foods, food preblends or mixes for home or food service use, such as preblends for soups or gravy, dessert mixes, dinner mixes, baking mixes such as bread mixes, and cake mixes, and baking flour.

The present invention is further illustrated by the following non-limiting examples where all parts, percentages, proportions, and ratios are by weight, and all temperatures are in ° C. unless otherwise indicated:

EXAMPLE 1

Encapsulation of a Water Soluble, Sensitive Pharmaceutical Component

Acetylcysteine may be encapsulated by feeding a prepared blend of 96.3% corn starch, 3% low density polyethylene (LDPE) and 0.7% glycerin-monostearate (GMS) at a rate of 4.0 kg/h into a first feed barrel of a co-rotating twill screw extruder. In addition to the corn starch/GMS/LDPE mix, vegetable oil was fed into barrel #1 via a piston pump at a rate of 0.17 kg/h. Water was added to the mix at a rate of 1.1 kg/h via a piston pump through a liquid injection port of barrel #2. The extruder used was a Werner and Pfleiderer ZSK 25 with a screw diameter of 25 mm. The screw configuration and barrel temperature profile used was as described in FIG. 2. The extruder used had nine barrel sections. Each barrel section was equipped with bores to either heat or cool the individual barrels. Barrels 1 and 2 were cooled with tap water, barrel 3 was heated at 100° C. and barrels 4 and 5 were heated at 120° C. using heat stable thermo-oil, that was temperature controlled via two separate control units (SINGLE, GERMANY). Barrels 6, 7, 8 and 9 were tap water cooled at a constant temperature of 15° C.

Screw elements are arranged in a way to first convey the material from the feed barrel into subsequent closed barrels to allow addition and mixing of additional ingredients, while increasing the degree of fill to effectively heat the product through conductive heat transfer with the barrel walls. Barrels 3, 4 and the first part of barrel 5 are dedicated for heating the product. The screw configuration in these barrels is designed to maintain sufficient residence time so as to at least partially gelatinize the starch while simultaneously admixing the additional ingredients at sufficiently low viscosity so as to prevent substantial dextrinization of the starch. This is accomplished through the high moisture content (30.9%) and addition of oil (3.2%) and emulsifier (0.7%) in the added amounts, combined with sufficiently low screw rpm, which was held constant at 150 rpm.

High temperature in Barrel #5 may also allow sufficient moisture to be removed in order to obtain sufficiently low moisture to enable sufficient forming and cutting of the extrudate after exiting the extruder. It has been experienced, that relatively high moisture contents in the extrudate, for example values greater than about 30% tend to cause the material to be difficult to shape at the die into stable ropes. Furthermore, it has been found that softer and moister ropes are extremely difficult to cut after exiting the extruder, particularly at the die face using high speed rotating cutters. Therefore, it has been found advantageous to cook the starch at relatively high moisture contents to prevent dextrinization and over shearing, but reduce the moisture level prior to extruding to prevent the extrudate from collapsing and to ensure adequate forming.

It has been observed that dextrinization during extrusion will result in dextrin formation during the cooking process and cause the mass to be sticky at the extruder exit and may severely reduce the ability to cut the mass into discrete particles. It has been therefore an additional objective of this invention to minimize dextrinization and reduce moisture after cooking to enable the forming and cutting of discrete particles that after cooling and drying exhibit specific release properties of the encapsulant.

After reducing the moisture content of the plastizied mass, the mass is cooled down to a sufficiently low temperature in barrel 6. The screw elements are conveying elements, that may be staggered and thus provide extended residence time to increase the degree of fill and thus enable effective cooling.

Barrel 7 was held open for the addition of the encapsulant and was kept at a temperature of 15 degrees C. The product temperature at this barrel was 25° C. The screw elements were high pitch elements to allow sufficient intake of the material. An additional supporting barrel insert may be used to prevent product build up while it is being conveyed through this open barrel section. Acetylcysteine was fed into barrel 7 a rate of 0.4 kg/h, conveyed into the subsequent barrel and mixed into the matrix material using distributive low shear mixing elements. The encapsulant was fed at about room temperature into the extruder. The choice of screw elements and their configuration in this section is such that the elements must not introduce high mechanical energy, but still mix the encapsulant into the matrix. This can be accomplished, for example, through the use of so-called distributive mixing elements that provide axial leakage flow in combination with a chopping action and a minimum of kneading action.

The last 2 to 3 l/d screw length may be used to generate sufficient pressure to extrude the material through the die openings. The die used comprised 20 openings, arranged in two circles of ten bores, each having a cylindrical bore of 2 mm over a length of 4 mm and a subsequent narrow opening of 1 mm over a land length of 2 mm. The larger opening of the first part of the dies is critical to prevent substantial energy dissipation within the die through overshearing that would result in an increase of the product temperature and thus cause a thermal destruction of the encapsulant. Additionally, too narrow die channels cause higher pressures before the die and may result in overheating of the product in the last barrel despite the cooling. The product temperature of the matrix at the encapsulant feeding point was about 25° C. The product temperature at the exit die was 52° C. The pressure at the die was 80 bar. The mean residence time of the encapsulant from the feed location to the die exit was about 35 seconds. On a calculated basis, the maximum flow rate of extrudate per die area is 0.361 kg/hr per mm$^2$, based upon the total amount of components added to the extrudate.

Immediately after the extrudate exited the extruder, it was cut into distinct pellets of approximately 1 mm length, allowing the pellets to have approximately spherical dimensions. The extrudate may be optionally sprayed with oil or other film-building substances while being cut. After extrusion, the extruded pellets were dried at 30° C. for about 12 hours to a final moisture content of approximately 8% by weight.

The dried pellets were stable in water for 16 hours and the acetylcystein may be sufficiently encapsulated within the matrix to allow controlled release under appropriate conditions. Appropriate release conditions may be a release in an aqueous or gastric juice environment that allows a release of the encapsulant of no more than from about 10% in about 1 hour to no less than about 90% in about 24 hours.

EXAMPLE 2 AND COMPARATIVE EXAMPLE 1

Encapsulation of a Heat Sensitive Component Prior and After Heat Treatment

In this example, the effect of addition of the encapsulant prior to and after heat treatment was evaluated. The extruder used was the same as used in Example 1 and screw rpm was 150. A blend of 99.7% by weight starch with 0.3% GMS was fed at 4.0 kg/hr into barrel #1. Vegetable oil was fed at a rate of 0.39 kg/h into barrel #1. Ascorbic acid was fed at a rate of 1.15 kg/h into barrel 1 (Comparative Example 1) and was exposed to the following barrel temperature profile: Barrel 1 (15° C.), Barrel 2 (15° C.), Barrel 3 (120° C.), Barrel 4 (140° C.), Barrel 5 (140° C.), Barrel 6 (15° C.), Barrel 7 (15° C.), Barrel 8 (15° C.), Barrel 9 (15° C.). On a calculated basis, the maximum flow rate of extrudate per die area is 0.352 kg/hr per mm$^2$, based upon the total amount of components added to the extruder. Analysis of ascorbic acid after extrusion resulted in a 72.3% loss.

The same extrusion conditions were used in Example 2, except that ascorbic acid was fed into barrel #7 at a product temperature of about 20° C. and subsequent analysis resulted in only a 12.2% loss of ascorbic acid. After extrusion, the extruded pellets were dried at 30° C. for about 12 hours and had a final moisture content of approximately 8%. The dried pellets were stable in water for 16 hours and the ascorbic Acid may be sufficiently encapsulated within the matrix to allow controlled release under appropriate release conditions.

EXAMPLE 3

Encapsulation of a Heat Sensitive Fat Soluble Component

In this example, a heat-sensitive fat soluble component was encapsulated. The extruder used was the same as used in Example 1 and the screw rpm was 150. A blend of 96.7% by weight starch, 3% by weight LDPE and 0.3% by weight GMS was fed at 4.0 kg/hr into barrel #1. Vegetable oil was fed at a rate of 0.16 kg/h into barrel #1. Following barrel temperature profile was used: Barrel 1 (15° C.), Barrel 2 (15° C.), Barrel 3 (120° C.), Barrel 4 (140° C.), Barrel 5 (140° C.), Barrel 6 (15° C.), Barrel 7 (15° C.), Barrel 8 (15° C.), Barrel 9 (15° C.). The encapsulant salicylic acid may be fed at a rate of 1.15 kg/h into barrel 7 at a temperature of 20° C. The encapsulant was mixed into the matrix and extruded into ropes that were cut at the die into distinct spherical pellets having a diameter of about 1 mm. On a calculated basis the maximum flow rate of extrudate per die area is 0.338 kg/hr per mm$^2$, based upon the total amount of components added to the extruder. After extrusion, the extruded pellets were dried at 30° C. for about 12 hours to a final moisture content of approximately 8% by weight. The dried pellets were stable in water for 16 hours and the salicylic acid may be sufficiently encapsulated within the matrix to allow controlled release under appropriate conditions.

EXAMPLES 4 TO 8 AND COMPARATIVE EXAMPLE 2

Encapsulation of a Water Soluble and Heat Sensitive Substance into Various Matrices In Examples 4 through 8 and Comparative Example 2, the extruder of Example 1 was used to encapsulate a water soluble, heat sensitive substance, ascorbic acid, in various matrices using various extrusion conditions. A release-rate controlling component was employed in Examples 4 to 8 but not in Comparative Example 2. The rate of release of the ascorbic acid from the matrices into meta-phosphoric acid was evaluated. The matrix compositions, extrusion conditions, and release results are presented in Table 1:

TABLE 1

Matrix Compositions, Extrusion Conditions, and Release Results

| Example | Units | Comparative Example 2 | 4 | 5 | 6 | 7 | 8 |
|---|---|---|---|---|---|---|---|
| Ingredient (Preblend) | kg | M1 | M3 | M4 | M6 | M6 (AA/oil) | M9 (Hydroph.) |
| Corn Starch | | 4.00 | 3.00 | 3.00 | 3.00 | 3.00 | 0.00 |

TABLE 1-continued

Matrix Compositions, Extrusion Conditions, and Release Results

| Example | Units | Comparative Example 2 | 4 | 5 | 6 | 7 | 8 |
|---|---|---|---|---|---|---|---|
| Wheat Gluten | | 0.00 | 1.00 | 1.00 | 1.00 | 1.00 | 0.00 |
| Gelatin | | 0.00 | 0.00 | 0.00 | 0.50 | 0.50 | 0.00 |
| Wax | | 0.00 | 0.50 | 1.00 | 0.50 | 0.50 | 0.00 |
| GMS | | 0.00 | 0.04 | 0.04 | 0.04 | 0.04 | 0.00 |
| Hydrophilic Corn Starch | | 0.00 | 0.00 | 0.00 | 0.00 | 0.00 | 4.00 |
| Total | | 4.00 | 4.54 | 5.04 | 5.04 | 5.04 | 4.00 |
| Extrusion Conditions | | | | | | | |
| Matrix Preblend Feed Rate | kg/hr | 4.00 | 3.50 | 3.50 | 3.50 | 3.50 | 3.50 |
| Oil Feed Rate | kg/hr | 0.00 | 0.00 | 0.16 | 0.00 | 0.00 | 0.00 |
| Water Feed Rate | kg/hr | 1.05 | 1.82 | 1.32 | 2.38 | 1.15 | 1.15 |
| Ascorbic Acid/oil premix | | | | | | | |
| Oil | kg/hr | 0.00 | 0.00 | 0.00 | 0.00 | 1.12 | 0.00 |
| Ascorbic acid | kg/hr | 0.00 | 0.00 | 0.00 | 0.00 | 2.00 | 0.00 |
| Screw rpm | min$^{-1}$ | 150 | 150 | 160 | 150 | 150 | 150 |
| Temp. Barrel 1 | °C. | 15 | 15 | 15 | 15 | 15 | 15 |
| Temp. Barrel 2 | °C. | 15 | 15 | 15 | 15 | 15 | 15 |
| Temp. Barrel 3 | °C. | 120 | 120 | 150 | 140 | 140 | 140 |
| Temp. Barrel 4 | °C. | 150 | 150 | 165 | 165 | 165 | 165 |
| Temp. Barrel 5 | °C. | 150 | 150 | 165 | 165 | 165 | 165 |
| Temp. Barrel 6 | °C. | 15 | 15 | 15 | 15 | 15 | 15 |
| Temp. Barrel 7 | °C. | 15 | 15 | 15 | 15 | 15 | 15 |
| Temp. Barrel 8 | °C. | 15 | 15 | 15 | 15 | 15 | 15 |
| Temp. Barrel 9 | °C. | 15 | 15 | 15 | 15 | 15 | 15 |
| Pressure | bar | 90 | 40 | 45 | 15 | — | 50 |
| Die Temperature | °C. | 62 | 57 | 86 | 66 | — | 71 |
| Other Data | Wt. % | 7.1 | 3.9 | 7.1 | 8.57 | 31.8 | 3.74 |
| % added Ascorbic Acid (Dry Basis) | | | | | | | |
| Weight % Ascorbic Acid Released in Meta Phosphoric Acid | Wt. % | | | | | | |
| 0 minutes | | 0.00 | 0.00 | 0.00 | 0.00 | 0.00 | 0.00 |
| 30 minutes | | 56.00 | 73.28 | 3.37 | 15.85 | 45.02 | 41.91 |
| 60 minutes | | 80.21 | 86.39 | 5.11 | 26.29 | — | — |
| 90 minutes | | 91.72 | — | 5.52 | 32.34 | 73.08 | — |
| 120 minutes | | 94.96 | — | 6.49 | 33.49 | 77.40 | 82.63 |
| 240 minutes | | 107.42 | 94.61 | 7.27 | 34.77 | 92.67 | 97.39 |

The ascorbic release data in meta-phosphoric acid has been corrected for destruction of ascorbic acid by the meta-phosphoric acid over time by dividing the analytical value by a correction factor ranging from 1.0 (at 0 minutes) to 0.906 (at 240 minutes).

Figure 6:
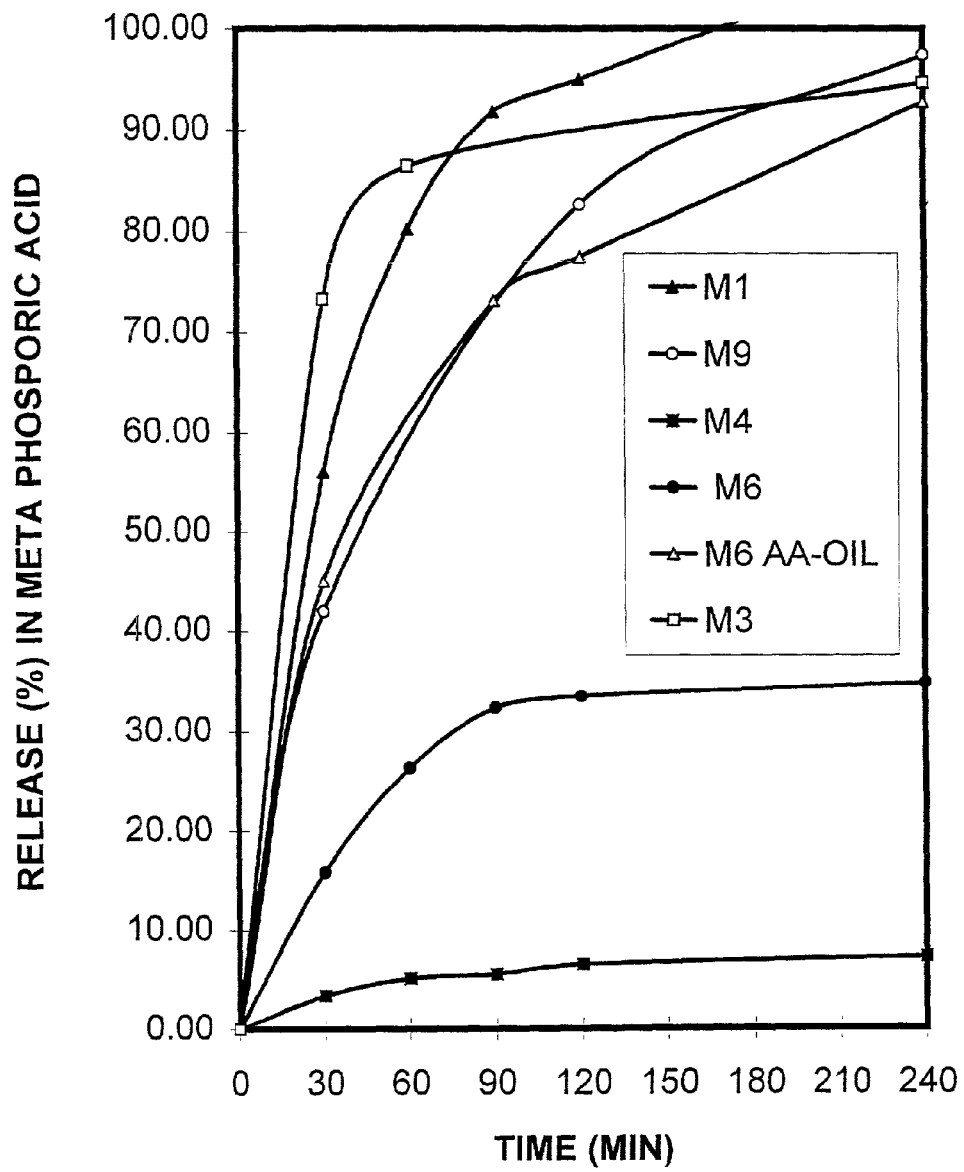
FIG. 6 shows release data for encapsulated ascorbic acid from various matrix compositions.

The release data is also presented in graphical form in FIG. 6 where the percentage of encapsulant released in meta-phosphoric acid is plotted as a function of time. As demonstrated by the data shown in Table 1 and FIG. 6, in Comparative Example 2 (M1) pure starch does not present a sufficient matrix for encapsulation, because the time to release 100% of the encapsulant is too short. Therefore, at least one additional component is added to control the hydrophobicity and control the release of the encapsulant. As shown in Examples 4-8, the addition of matrix components such as lipids and/or proteins, shifts the encapsulant retention properties substantially towards longer retention times.

EXAMPLE 9

Encapsulation of Heat Sensitive Substances into Various Matrices

Heat sensitive encapsulants or components may be encapsulated into various matrices using the extruder, screw configuration, barrel configuration, screw speed (150 rpm), and die configuration of Example 1. The barrel temperature profile which may be used is: Barrel 1 (15° C.), Barrel 2 (15° C.), Barrel 3 (120° C.), Barrel 4 (140° C.), Barrel 5 (140° C.), Barrel 6 (35° C.), Barrel 7 (35° C.), Barrel 8 (35° C.), Barrel 9 (35° C.). In another embodiment, the barrel temperature in barrels 4 and 5 may be 150° C.

The ingredients and their concentrations which may be used in matrices to vary the release rate of the encapsulant are presented in Table 2:

TABLE 2

Matrix Components and Concentrations

| Matrix Component | from low | to mid | to max | Function |
|---|---|---|---|---|
| Carbohydrates | | | | |
| Plant Starch | 1 | 40 | 99 | base matrix material |
| Cyclodextrin | 0 | 10 | 60 | affects molecular encapsulation |
| Hydrophobic starch | 0 | 20 | 40 | affects hydrophobicity of matrix |
| Protein sources | | | | |
| Wheat Gluten | 0 | 10 | 50 | affects tolerable oil/fat addition |
| Soy Protein Conc. | 0 | 10 | 50 | affects tolerable oil/fat addition |

TABLE 2-continued

Matrix Components and Concentrations

| Matrix Component | from low | to mid | to max | Function |
|---|---|---|---|---|
| Casein | 0 | 10 | 50 | affects tolerable oil/fat addition |
| Gelatin | 0 | 10 | 30 | affects water binding properties and affects oil addition |
| Hydrocolloid sources | | | | |
| Guar | 0 | 5 | 30 | increases water binding capacity |
| Pectin | 0 | 5 | 30 | increases water binding capacity |
| Gum Arabic | 0 | 5 | 30 | increases water binding capacity |
| Lipids and Lipoids | | | | |
| veg. Oil | 3 | 10 | 20 | affects hydrophobicity of matrix |
| Paraffin | 0 | 5 | 20 | affects hydrophobicity of matrix |
| GMS | 1 | 5 | 10 | affects hydrophobicity of matrix |
| Shellac | 0 | 5 | 20 | affects hydrophobicity of matrix |
| Synthetic Polymers | | | | |
| LDPE | 0 | 2 | 6 | affects hydrophobicity of matrix |
| Polyvinylpyrollidone | 20 | 40 | 60 | plasticizer, allows molecular dispersion |

A blend of starch and/or plasticizer, and one or more of the listed components may be fed at 4.0 kg/hr into barrel #1. Vegetable oil or any other hydrophobic substance may be fed at a rate of 0.1 to about 3 kg/h into barrel #1. The encapsulant may be fed at a rate of 0.1 to 3 kg/h into barrel 7 at a temperature of about 20° C. The encapsulant may be mixed into the matrix and extruded into ropes that are cut at the die into distinct spherical pellets having a diameter of about 1 mm. After extrusion, the extruded pellets may be dried at 30° C. for sufficient time, such as about 12 hrs to a final moisture content of approximately 8% by weight. The dried pellets may be stable in aqueous solution for sufficient time, for example, 16 hrs and the encapsulant may be sufficiently encapsulated within the matrix to allow controlled release under appropriate conditions.

The encapsulant may be pretreated before the encapsulation using a sprayable material, such as an alcoholic solution of zein, a chitin-based material, shellac, paraffin or a similar coating material. For this purpose, the encapsulant may be placed into a rotating coating drum, commonly used in the candy industry. The coating composition, for example zein at a concentration of, for example 10% zein may be applied as a coating onto the surface of the encapsulant. The drum may be treated with warm air to facilitate drying of the solvent. After drying the coated encapsulant, it may be added to the extruder as described in Example 1. The additional coating may additionally control the rate of release of the encapsulant after the matrix has been dissolved and the encapsulant is dispersed in the environment for its expected action.

After extrusion under the described process conditions, the obtained pellets may be coated with a film of variable thickness to delay the access of either aqueous or digestive liquids to the matrix and thus delay solution of the matrix. For this purpose, a sprayable material may be used, such as an alcoholic solution of zein, a chitin-based material, shellac, paraffin or similar film-forming or coating substance. The extruded pellets may be placed into a rotating coating drum, a device commonly used in the candy and confectionery industry and a solution of about 10% by weight zein and about 90% by weight isopropyl alcohol or other solvent may be applied as a coating onto the surface of the encapsulant. The drum may be treated with warm air to facilitate drying and removal of the solvent. The additional coating may additionally control the rate and time of release of the encapsulant and may provide complete control over the release properties of the encapsulant. It is expected, that the release properties follow the schematic diagram in FIG. 5.

What is claimed is:

1. An encapsulated product comprising discrete, solid particles having a substantially uniform shape and a diameter of up to about 10 mm, wherein each particle comprises:
   a plasticized matrix material comprising a partially gelatinized starch in an amount of about 40% or more based on the weight of the final product, the plasticized matrix material comprising starch having substantially intact molecules,
   at least one component for controlling the rate of release of the encapsulant,
   at least one plasticizer comprising water, and
   an encapsulant in an amount of from about 1% to about 85% based upon the weight of the plasticized matrix material, the encapsulant dispersed throughout the plasticized matrix material and comprising at least one pharmaceutical component, neutraceutical component, nutritional component, fragrance component, or biologically active component,
   wherein the encapsulant and plasticized matrix material form an at least substantially homogenous mixture.

2. An encapsulated product comprising discrete, solid particles having a substantially uniform shape and a diameter of up to about 10 mm, wherein each particle comprises:
   a plasticized matrix material in an amount of about 40% or more based on the weight of the final product, the plasticized matrix material comprising starch having substantially intact molecules,
   at least one component for controlling the rate of release of the encapsulant,
   at least one plasticizer, and
   an encapsulant in an amount of from about 1% to about 85% based on the weight of the starch, the encapsulant dispersed throughout the plasticized matrix material and comprising at least one pharmaceutical component, neutraceutical component, nutritional component, fragrance component, or biologically active component,
   wherein the encapsulant and plasticized matrix material form an at least substantially homogenous mixture, and
   wherein said encapsulant is coated with a film-forming material prior to dispersion within said plasticized matrix material.

3. An encapsulated product according to claim 1 wherein said particles are in the form of a tablet, or a pellet.

4. An encapsulated product according to claim 3 wherein said particles are coated with a film-forming material.

5. An encapsulated product according to claim 1 wherein said at least one release-rate controlling component is a hydrophobic component.

6. An encapsulated product according to claim 5 wherein said hydrophobic component is at least one member selected from the group consisting of fats, oils, waxes, fatty acids, emulsifiers, polyolefins, paraffin, polyvinyl acetate and derivatives thereof, and modified starches.

7. An encapsulated product according to claim 1 which has a specific density of from about 800 g/liter to about 1500 g/liter.

8. An encapsulated product according to claim 1 wherein the length-to-diameter ratio of said particles is from about 0.1 to about 10.

9. An encapsulated product according to claim 1 wherein said particles have a substantially non-expanded, substantially non-cellular structure.

10. An encapsulated product according to claim 1 wherein said encapsulant is released in an aqueous or gastric juice environment in an amount of no more than from about 10% in about 1 hour to no less than about 90% in about 24 hours.

11. An encapsulated product according to claim 1 wherein:
the amount of the plasticized matrix material is from about 60% by weight to about 95% by weight, based upon the weight of the final product, and
the amount of said at least one component used to control the rate of release of the encapsulant is from about 5% by weight to about 50% by weight, based upon the weight of the matrix material.

12. An encapsulated product according to claim 11 wherein said particles have a diameter of from about 0.5 mm to about 5 mm and a length-to-diameter ratio of about 0.5 to about 2.

13. An encapsulated product according to claim 1 wherein said plasticized matrix material comprises durum wheat or semolina.

14. An encapsulated product according to claim 1 wherein said encapsulant is at least one member selected from the group consisting of antioxidants, phytochemicals, hormones, microorganisms, prebiotics, probiotics, enzymes, formulations containing zidovudine, macromolecular polypeptides, aromatic nitro and nitroso compounds and their metabolites useful as anti-viral and anti-tumor agents, HIV protease inhibitors, antibiotics, viruses, steroids, oligopeptides, dipeptides, amino acids, fragrance components, adenosine derivatives, sulfated tannins, monoclonal antibodies, and metal complexes of water-soluble texathyrin.

15. An encapsulated product according to claim 1 wherein said plasticized matrix material further comprises at least one member selected from the group consisting of cyclodextrins, dextrins, monosaccharides, disaccharides, polyvinylpyrrolidone, copolymers of N-vinylpyrrolidone and vinyl acetate, polyvinyl alcohol, cellulose esters, cellulose ethers, and polyethylene glycol.

16. An encapsulated product comprising:
discrete, solid particles having a substantially uniform shape wherein each particle comprises:
a plasticized matrix material comprising a partially gelatinized starch in an amount of about 40% or more by weight, based on the weight of the final encapsulated product, wherein said plasticized matrix material comprises starch having substantially intact molecules,
an encapsulant dispersed throughout the plasticized matrix material, and
at least one component for controlling the rate of release of the encapsulant,
wherein said encapsulant comprises at least one pharmaceutical component, neutraceutical component, nutritional component, fragrance component, or biologically active component,
wherein said matrix material comprises at least one member selected from the group consisting of durum wheat, semolina, wheat flour, wheat gluten, soy protein, hydrocolloids, casein, and gelatin, and at least one plasticizer comprising water,
wherein the encapsulant and plasticized matrix material form an at least substantially homogeneous mixtures, and
wherein the amount of said encapsulant is from about 1% by weight to about 85% by weight, based upon the weight of the matrix material.

17. An encapsulated product comprising:
discrete, solid particles having a substantially uniform shape wherein each particle comprises:
a plasticized matrix material in an amount of about 40% or more by weight, based on the weight of the final encapsulated product, wherein said plasticized matrix material comprises starch which has substantially intact molecules,
an encapsulant dispersed throughout the plasticized matrix material, and
at least one component for controlling the rate of release of the encapsulant,
wherein said encapsulant comprises at least one pharmaceutical component, neutraceutical component, nutritional component, fragrance component, or biologically active component,
wherein said matrix material comprises at least one member selected from the group consisting of durum wheat, semolina, wheat flour, wheat gluten, soy protein, hydrocolloids, casein, and gelatin, and at least one plasticizer,
wherein the encapsulant and plasticized matrix material form an at least substantially homogeneous mixture,
wherein the amount of said encapsulant is from about 1% by weight to about 85% by weight, based upon the weight of the matrix material, and
wherein said encapsulant is coated with a film-forming material prior to dispersion within said plasticized matrix material.

18. An encapsulated product according to claim 16 wherein said particles are in the form of a tablet, or a pellet.

19. An encapsulated product according to claim 16 wherein said particles are spherical.

20. An encapsulated product according to claim 18 wherein said particles are coated with a film-forming material.

21. An encapsulated product according to claim 16 wherein said at least one release-rate controlling component is a hydrophobic component.

22. An encapsulated product according to claim 21 wherein said hydrophobic component is at least one member selected from the group consisting of fats, oils, waxes, fatty acids, emulsifiers, polyolefins, paraffin, polyvinyl acetate and derivatives thereof, and modified starches.

23. An encapsulated product according to claim 16 which has a specific density of from about 800 g/liter to about 1500 g/liter.

24. An encapsulated product according to claim 16 wherein the length-to-diameter of said particles is from about 0.1 to about 10.

25. An encapsulated product according to claim 16 wherein said particles have a substantially non-expanded, substantially non-cellular structure.

26. An encapsulated product according to claim 16 wherein said encapsulant is released in an aqueous or gastric juice environment in an amount of no more than from about 10% in about 1 hour to no less than about 90% in about 24 hours.

27. An encapsulated product according to claim 16 wherein the amount of said at least one component for controlling the rate of release of the encapsulant is up to about 70% by weight, based on the weight of the matrix material.

28. An encapsulated product according to claim 16 wherein said particles have a diameter of from about 0.5 mm to about 5 mm and a length-to-diameter ratio of about 0.5 to about 2.

29. An encapsulated product according to claim 16 wherein said matrix material comprises at least one member selected from the group consisting of durum wheat, semolina, wheat flour, wheat gluten, and soy protein.

30. An encapsulated product according to claim 16 wherein said matrix material comprises at least one member selected from the group consisting of durum wheat and semolina.

31. An encapsulated product according to claim 16 wherein said discrete, solid particles have a diameter of up to about 10 mm.

32. An encapsulated product according to claim 16 wherein said encapsulant is at least one member selected from the group consisting of antioxidants, phytochemicals, hormones, microorganisms, prebiotics, probiotics, enzymes, formulations containing zidovudine, macromolecular polypeptides, aromatic nitro and nitroso compounds and their metabolites useful as anti-viral and anti-tumor agents, HIV protease inhibitors, antibiotics, viruses, steroids, oligopeptides, dipeptides, amino acids, fragrance components, adenosine derivatives, sulfated tannins, monoclonal antibodies, and metal complexes of water-soluble texathyrin.

33. An encapsulated product according to claim 16 wherein said plasticized matrix material further comprises at least one member selected from the group consisting of cyclodextrins, dextrins, monosaccharides, disaccharides, polyvinylpyrrolidone, copolymers of N-vinylpyrrolidone and vinyl acetate, polyvinyl alcohol, cellulose esters, cellulose ethers, and polyethylene glycol.

34. An encapsulated product according to claim 16 wherein:
the amount of the matrix material is from about 60% by weight to about 95% by weight, based upon the weight of the final product, and
the amount of said at least one component used to control the rate of release of the encapsulant is from about 5% by weight to about 50% by weight, based upon the weight of the matrix material.

35. An encapsulated product according to claim 16 wherein said encapsulant comprises at least one member selected from the group consisting of enzymes and microorganisms.

36. An encapsulated product comprising discrete, solid particles having a substantially uniform shape wherein each particle comprises:
an encapsulant in an amount of about 5% by weight to about 20% by weight, based upon the weight of the matrix material, dispersed throughout a plasticized matrix material comprising starch which has substantially intact molecules, said matrix material comprising at least one member selected from the group consisting of durum wheat, semolina, vital wheat gluten, soy protein, hydrocolloids, casein, and gelatin, and at least one plasticizer comprising water,
wherein said encapsulant comprises at least one pharmaceutical component, neutraceutical component, nutritional component, fragrance component, or biologically active component,
wherein the encapsulant and plasticized matrix material form an at least substantially homogeneous mixture,
wherein the amount of said encapsulant is from about 3% by weight to about 50% by weight, based upon the weight of the matrix material, and
wherein the amount of said matrix material is about 40% or more by weight, based upon the weight of the final encapsulated product.

37. An encapsulated product according to claim 36 wherein said encapsulant comprises at least one member selected from the group consisting of enzymes and microorganisms.

38. An encapsulated product according to claim 1, comprising about 3% by weight to about 50% by weight of the encapsulant, based upon the weight of the matrix material.

39. An encapsulated product according to claim 1, comprising about 5% by weight to about 20% by weight of the encapsulant, based upon the weight of the matrix material.

40. An encapsulated product according to claim 1, wherein the encapsulant is in liquid form.

41. An encapsulated product according to claim 16, comprising about 3% by weight to about 50% by weight of the encapsulant, based upon the weight of the matrix material.

42. An encapsulated product according to claim 16, comprising about 5% by weight to about 20% by weight of the encapsulant, based upon the weight of the matrix material.

43. An encapsulated product according to claim 36 wherein said matrix material comprises semolina or durum wheat.

44. An encapsulated product according to claim 1, comprising said plasticized matrix material in an amount of from about 60% by weight to about 95% by weight based upon the weight of the final encapsulated product.

45. An encapsulated product according to claim 16 comprising from about 60% by weight to about 95% by weight of the matrix material, based upon the weight of the final encapsulated product.

46. An encapsulated product according to claim 36 comprising from about 60% by weight to about 95% by weight of the matrix material, based upon the weight of the final encapsulated product.

47. An encapsulated product according to claim 1 wherein said plasticized matrix material comprises at least one member selected from the group consisting of durum wheat, semolina, wheat flour, wheat gluten, native or modified starches, soy protein, casein, and gelatin.

48. An encapsulated product according to claim 1 wherein said plasticized matrix material comprises at least one member selected from the group consisting of durum wheat, semolina, wheat flour, wheat gluten, native starches and modified starches.

49. An encapsulated product according to claim 2 wherein said plasticized matrix material comprises at least one member selected from the group consisting of durum wheat and semolina.

50. An encapsulated product according to claim 1 wherein at least a portion of the starch is not cooked.

51. An encapsulated product according to claim 1 wherein the starch is not cooked or is cooked so that the specific energy input during cooking is below about 100 Wh/kg.

* * * * *